United States Patent
Lopreato

(10) Patent No.: US 8,680,017 B2
(45) Date of Patent: *Mar. 25, 2014

(54) LARIAT APTAMER: APTAMER CANDIDATE EXCLUSION BY NUCLEASE DIGESTION

(76) Inventor: Gregory Francis Lopreato, Nederland, TX (US)

(*) Notice: Subject to any disclaimer, the term of this patent is extended or adjusted under 35 U.S.C. 154(b) by 294 days.

This patent is subject to a terminal disclaimer.

(21) Appl. No.: 13/026,244

(22) Filed: Feb. 12, 2011

(65) Prior Publication Data

US 2011/0251088 A1    Oct. 13, 2011

Related U.S. Application Data

(60) Provisional application No. 61/304,426, filed on Feb. 13, 2010.

(51) Int. Cl.
    *C40B 30/04*  (2006.01)
(52) U.S. Cl.
    USPC ............................................. 506/9
(58) Field of Classification Search
    None
    See application file for complete search history.

(56) References Cited

U.S. PATENT DOCUMENTS

2003/0119150 A1*  6/2003  Ankenbauer et al. ........ 435/91.2

OTHER PUBLICATIONS

Hannoush et al. (Nov. 29, 2004) Nucleic Acids Research vol. 32 pp. 6164 to 6175.*
Wang et al. (Aug. 24, 2004) Analytical Chemistry vol. 76 pp. 5605 to 5610.*
Bonnet et al. (Jul. 1998) PNAS USA vol. 95 pp. 8602 to 8606.*
Childs et al. (1976) Journal of Food Science vol. 41 pp. 652 to 655.*
Schmidt et al. (Oct. 27, 2004) Nucleic Acids Research vol. 32 pp. 5757 to 5765.*

* cited by examiner

*Primary Examiner* — Christian Boesen

(57) ABSTRACT

A method for identifying aptamers that bind to target molecules may include contacting an oligonucleotide library with target molecule and digesting unbound oligonucleotides with one or more endonucleases, one or more exonucleases, or one or more endonucleases in combination with one or more exonucleases. The unbound oligonucletides lend themselves to nuclease digestion because their flanking sequences are complementary and form predictable, terminal, secondary structure (a Lariat Aptamer). Bound molecules (aptamers) are protected from nuclease digestion and become enriched. A method for identifying aptamers may further include optionally subjecting selected aptamers to one or more rounds of selection under conditions of increased stringency. A method for identifying aptamers may include yet further amplifying selected aptamers. The described methods may be performed in a screen for identifying aptamers either alone or in combination with other methods typically employed in the art for selecting aptamers (such as, e.g., SELEX). Also contemplated herein are systems and kits for accomplishing the above.

16 Claims, 2 Drawing Sheets

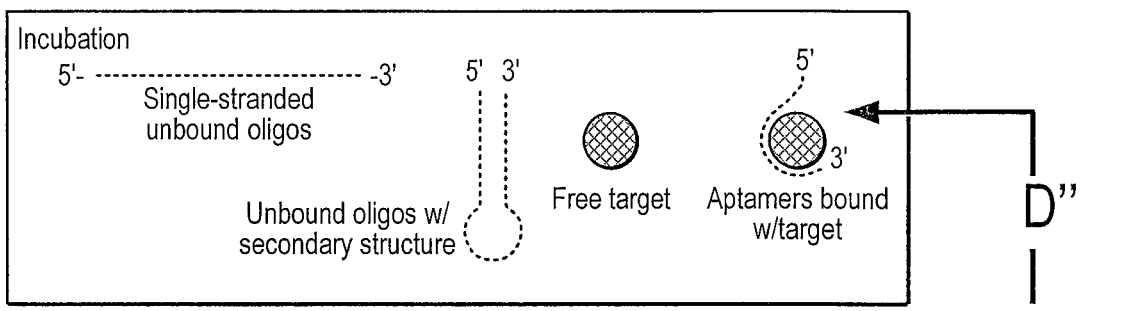
FIG. 1A
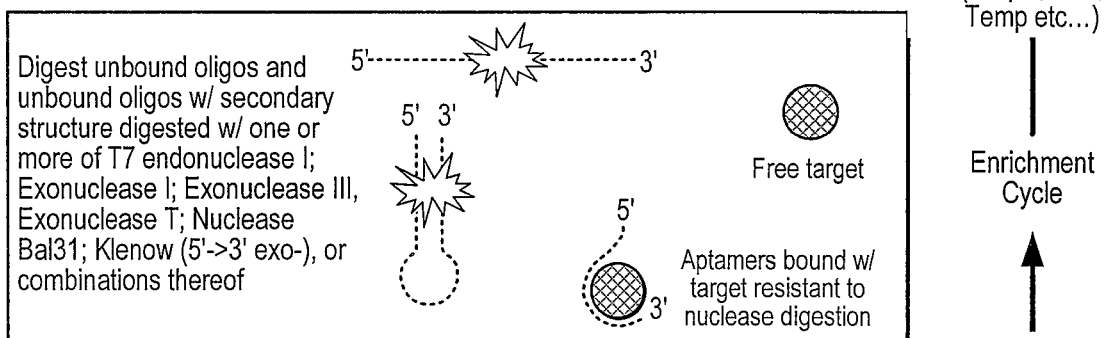
FIG. 1B
FIG. 1C
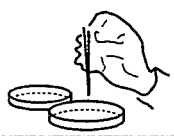
FIG. 1D
FIG. 1E

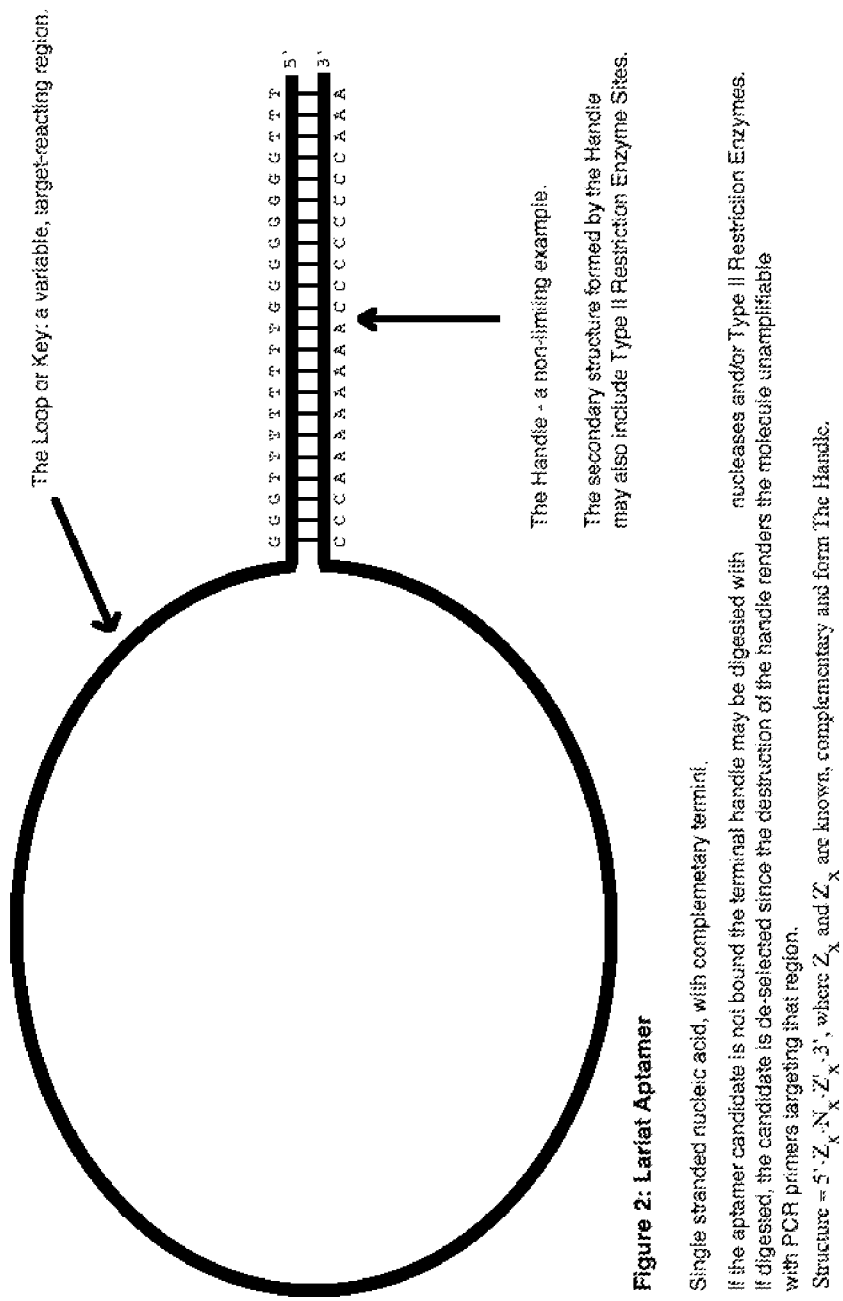

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthesized sequence

<400> SEQUENCE: 1
tttggggggg gttttttttg gg                                        22

<210> SEQ ID NO 2
<211> LENGTH: 22
<212> TYPE: DNA
<213> ORGANISM: Artificial Sequence
<220> FEATURE:
<223> OTHER INFORMATION: Synthesized sequence

<400> SEQUENCE: 2
cccaaaaaaa acccccccca aa                                        22

<210> SEQ ID NO 3
<211> LENGTH: 22
<212> TYPE: DNA
<213> ORGANISM: Artificial Sequence
<220> FEATURE:
<223> OTHER INFORMATION: Synthesized sequence

<400> SEQUENCE: 3
tttggggggg atcctttttg gg                                        22

<210> SEQ ID NO 4
<211> LENGTH: 22
<212> TYPE: DNA
<213> ORGANISM: Artificial Sequence
<220> FEATURE:
<223> OTHER INFORMATION: Synthesized sequence

<400> SEQUENCE: 4
cccaaaaagg atcccccca aa                                         22
```

LARIAT APTAMER: APTAMER CANDIDATE EXCLUSION BY NUCLEASE DIGESTION

PRIORITY CLAIM

This application claims the benefit of priority of U.S. Provisional Patent Application Ser. No. 61/304,426 entitled "THE LARIAT APTAMER: APTAMER CANDIDATE EXCLUSION BY THE INTRODUCTION OF NUCLEASE, DE-SELECTIVE VULNERABILITY IN THE STARTING MATERIAL", filed on Feb. 13, 2010.

BACKGROUND OF THE INVENTION

1. Field of the Invention

The present invention generally relates to the field of molecular biology. More specifically, the invention relates to systems and methods for rapid identification and enrichment of nucleic acid aptamers that bind to specific target molecules. Disclosed herein is a method that may be employed to select aptamers based on susceptibility to digestion by nucleases. In part, this is accomplished by beginning with a nucleic acid library that forms predictable, complementary, secondary structure at the termini. The secondary structures contain sequences that can be digested by nucleases. The library is incubated with a target of interest, and the unbound molecules are digested with nucleases, whereas the bound molecules are afforded protection from digestion by nucleases. With each round of subtraction, the complexity of the initial library is reduced until only the desirable aptamers remain: those that bind a target of interest.

2. Description of the Related Art

Aptamers are nucleic acid molecules having specific binding affinity to molecules through interactions other than classic Watson-Crick base pairing.

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Aptamers have a number of desirable characteristics for use as therapeutics (and diagnostics) including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial (therapeutic) leads. In vitro selection allows the specificity and affinity of the aptamer to be tightly controlled and allows the generation of leads against both toxic and non-immunogenic targets;

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers (most likely because aptamers cannot be presented by T-cells via the MHC and the immune response is generally trained not to recognize nucleic acid fragments;

3) Administration. Whereas all currently approved antibody therapeutics are administered by intravenous infusion (typically over 2-4 hours), aptamers can be administered by subcutaneous injection. This difference is primarily due to the comparatively low solubility and thus large volumes necessary for most therapeutic MAbs. With good solubility (>150 mg/ml) and comparatively low molecular weight (aptamer: 10-50 kDa; antibody: 150 kDa), a weekly dose of aptamer may be delivered by injection in a volume of less than 0.5 ml. Aptamer bioavailability via subcutaneous administration is >80% in monkey studies (Tucker et al., J. Chromatography B. 732: 203-212, 1999). In addition, the small size of aptamers allows them to penetrate into areas of conformational constrictions that do not allow for antibodies or antibody fragments to penetrate, presenting yet another advantage of aptamer-based therapeutics or prophylaxis;

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale synthesizer can produce upwards of 100 kg oligonucleotide per year and requires a relatively modest initial investment; and 5) Stability. Therapeutic aptamers are chemically robust. They are intrinsically adapted to regain activity following exposure to heat, denaturants, etc. and can be stored for extended periods (>1 yr) at room temperature as lyophilized powders. In contrast, antibodies must be stored refrigerated.

SELEX is a very powerful and novel technique used to search (i.e., pan) for aptamers exhibiting high-affinity and specific binding to target molecules of biomedical interest. SELEX searches a very large, random sequence oligonucleotide library (on the order of $10^{12}$ to $10^{15}$) for molecules exhibiting high-affinity binding to defined molecular targets. The small number of selected (i.e., high binding affinity) oligonucleotides can be geometrically amplified using the polymerase chain reaction (PCR) in a few weeks (or days with the use of robotics). Through a "survival of the fittest" sequential screening strategy (i.e., those having the highest binding affinity or catalytic activity) identification of novel aptamers can be accomplished rapidly in vitro using SELEX.

Despite its utility, SELEX is a laborious process requiring the physical separation of target bound aptamers and multiple rounds of sequential selection and amplification (Gold et al., 1995; Cox et al., 2002a, 2002b; Bruno and Kiel, 1999, 2002; Vivekananda and Kiel, 2006). The present invention seeks to exclude, by nuclease digestion, the number of candidate aptamers that are carried forward in sequential rounds of selection, thereby reducing the required number of selection rounds and increasing the likelihood that the surviving candidates are in fact aptamers that bind strongly to the target of interest.

SUMMARY OF THE INVENTION

In an embodiment, a method of identifying nucleic acid aptamers for a target molecule may include obtaining an at least partially purified target molecule, obtaining a nucleic acid ligand library, mixing the target molecule with the nucleic acid ligand library and binding the target molecule to one or more aptamers present in the nucleic acid ligand library, and digesting unbound nucleic acid molecules with one or more endonucleases (including restriction enzymes), with one or more exonucleases, with one or more endonuclease in combination with one or more exonucleases, including less discriminate nucleases like DNases and RNases which may be both endo- and exo-nucleases.

In an embodiment, a method of identifying nucleic acid aptamers for a target molecule may include obtaining an at least partially purified target molecule, obtaining a nucleic acid ligand library, mixing the target molecule with the nucleic acid ligand library and binding the target molecule to one or more aptamers molecules present in the nucleic acid ligand library, separating the aptamers bound to the target molecule from at least a portion of the unbound nucleic acid molecules, wherein said separating step is accomplished by: digesting unbound oligonucleotides, or digesting unbound oligonucleotides in combination at least one physical separation means, liberating the target molecule from the aptamers, and amplifying the aptamers.

Still further embodiments concern kits suitable for the purpose of performing a screen for aptamers that bind to a molecule of interest. The kits include, in at least a first suitable container, a suitable oligonucleotide library, one or more nucleases, in conjunction with instructions for use in performing a screen for aptamers that bind to a molecule of interest. A kit may optionally further contain one or more appropriate binding buffers, and/or one or more buffers suitable to enable activity of the provided nucleases. The kit may further contain one or more reagents, including suitable buffer, enzymes and primers, for amplifying selected aptamers by PCR.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1 is an overview of a Knockdown Nuclease-Protected Aptamer Selection and Acquisition ("KN-PASA") previously described in U.S. Provisional Patent Application No. 60/903,243 and in U.S. patent application Ser. No. 12/033,522, which lends foundation to the present disclosure. Its inclusion is provided as a reference point. The figure is also substantially illustrative of Lariat Aptamer Selection, except that the sequence of the nucleotide library differs which provide many benefits.

FIG. 2 is an overview of the general structure and utility of the Lariat Aptamer performed in accordance with one embodiment. The structure includes complementary termini involved in secondary structure called the "handle". It also includes the variable region, the "Loop" or "Key", which is involved in binding the target of interest. Aptamer/target complexes are sterically inhibited from digestion by nucleases. Unbound aptamers are digested by nucleases at the handle, or even internally. Once digested, they are not amplifiable by PCR, since the PCR primers target the handle sequence. Since it benefits from a priori knowledge of a secondary structure at the termini, the Lariat Aptamer Technique is a much more powerful than KN-PASA as will be discussed below.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a linker" includes one or more linkers. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below, or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "aptamers" generally refers to nucleic acid molecules having specific binding affinity to target molecules through interactions other than classic Watson-Crick base pairing. Aptamers are usually identified by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. More specifically, aptamers can be broadly classified as either nucleic acid (DNA or RNA) aptamers, which consist of (usually short) strands of oligonucleotides, or peptide aptamers, which consist of a short variable peptide domain, attached at both ends to a protein scaffold. Aptamers, like peptides generated by phage display or monoclonal antibodies (MAbs), are capable of specifically binding to selected targets and, through binding, block or otherwise alter the function of the target molecule to which they bind. Aptamers are typically identified by an in vitro selection process (such as, e.g., SELEX) from pools of random sequence oligonucleotides. Aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). Aptamers have a number of desirable characteristics for use as therapeutics including high specificity and affinity, biological efficacy, and excellent pharmacokinetic properties. While it will readily appreciated by a practitioner of the art that peptide apatmers also exist, such aptamers are beyond the scope of the present description. Aptamers, their uses and manufacture are shown in U.S. Pat. Nos. 5,567,588; 5,582,981; 5,631,146; 5,756,291; 5,780,449; 5,792,613; 5,840,867; 5,861,501; 6,001,648; 6,111,095; 6,207,388; 6,225,058; 6,369,208; 6,423,493; 6,458,559; 6,515,120; 6,569,630; 6,706,481; 6,780,850; 6,858,390; 6,867,289; 6,949,379; 6,994,959, as well as U.S. Patent Appl. Publ. Nos. 2007/0027096; 2007/0020641; 2007/0009476; 2006/0281702; 2006/0264369; 2006/0257915; 2006/0257914; 2006/0205089; 2006/0193821; 2006/0183702; 2006/0172925; 2006/0148745; 2006/0128649; 2006/0121489; 2006/0105980; 2006/0105975; 2006/0088864; 2006/0084109; 2006/0068407; 2006/0030535; 2006/0024814; 2006/0018871; 2006/0014172; 2006/0008841; 2005/0282226; 2005/0282190; 2005/0260164; 2005/0250106; 2005/0239134; 2005/0233317; 2005/0222400; 2005/0214772; 2005/0176940; 2005/0159351; 2005/0142582; 2005/0124565; 2005/0123939; 2005/0106594; 2005/0096290; 2005/0089864; 2005/0078179; 2005/0053970; 2004/0265912; 2004/0253679; 2004/0253243; 2004/0249130; 2004/0242521; 2004/0180360; 2004/0137429; 2004/0137010; 20040132067: 2004/0110235; 2004/0086924; 2004/0053310; 2004/0023266; 2004/0022727; 2003/0219801; 2003/0175730; 2003/0175703; 2003/0162190; 2003/0138831; 2003/0119159; 2003/0108532; 2003/0064530; 2003/0027184; 2003/0022853; 2002/0197617; 2002/0127581; 2002/0115629; 2002/0037506; and 2001/0046674, all of which are hereby expressly incorporated by reference in their entirety as though fully set forth herein.

As used herein, the term "polynucleotide" generally refers to a naturally occurring, recombinant or synthetic polymer of nucleotides (which contain sugar groups, and either purine or pyrimidine bases) that are covalently linked by sequential phosphodiester bonds. There are generally two types of polynucleotide: ribonucleic acid (RNA) and deoxyribonucleic acid (DNA). The bases involved are adenine, guanine, cytosine, and thymine (abbreviated A, G, C. and T, respectively) or uracil (abbreviated U) (in the case of RNA). Some nucleic acids may be informational biomolecules (e.g., DNA), or act as agent (e.g., RNA) in causing that information to be expressed (e.g., as a protein, or by its involvement in RNA-interference). For the purposes of the present disclosure, the terms "polynucleotide" and "nucleic acid" may generally be used interchangeably.

As used herein, the terms "isolated polynucleotide" or "isolated nucleic acid" generally refer to a polynucleotide, or a fragment thereof, that is free of the genetic material that, in the naturally occurring genome of the organism from which the nucleic acid is derived, flank the polynucleotide. The term therefore encompasses, for example, a DNA fragment that is incorporated, using recombinant DNA methodologies, into a vector; into an autonomously replicating plasmid or virus; or into the genome of a prokaryote or eukaryote; or that exists as a separate molecule (e.g., an oligonucleotide, siRNA duplexes, a cDNA or a genomic or cDNA fragment produced by PCR or restriction endonuclease digestion) independent of other sequences. It also includes recombinant DNA that is part of a hybrid gene encoding additional polypeptide sequence(s) (e.g. fusion protein) or an adapter sequence.

As used herein, the term "substantially identical", when used in reference to a polynucleotide, generally refers to a polynucleotide, or a portion or fragment thereof, whose nucleotide sequence is at least 95%, 90%, 85% 80%, 70%, 60% or 50% identical to the nucleotide sequence of a reference polynucleotide. When used in reference to a polypeptide, the term generally refers to a polypeptide, or a fragment thereof, whose amino acid sequence is at least 95%, 90%, 85% 80%, 70%, 60% or 50% identical to the amino acid sequence of a reference polypeptide. For polypeptides, the length of comparison sequences will generally be at least about 5 amino acids, and may include the complete polypeptide sequence. For nucleic acids, the length of comparison sequences will generally be at least about 15 nucleotides, and may include the complete reference nucleic acid sequence. Sequence identity between two or more polypeptide or nucleic acid sequences is typically determined using sequence analysis software (e.g., Sequence Analysis Software Package of the Genetics Computer Group, University of Wisconsin Biotechnology Center) designed for this purpose. Such software matches similar sequences by assigning degrees of homology to various substitutions, deletions, substitutions, and other modifications. Conservative substitutions typically include substitutions within the following groups: Gly; Ala; Val, Ile, Leu; Asp, Glu, Asn, Gln; Ser, Thr; Lys, Arg; and Phe, Tyr.

As used herein, the term "polymerase chain reaction" (commonly referred to in the art as "PCR") generally refers to a method, or a modification thereof, for increasing the concentration of a segment of a target DNA sequence in a mixture of DNA containing the target sequence. Examples of PCR methods are shown in U.S. Pat. Nos. 4,683,195 4,683,202, and 4,965,188, all of which are incorporated herein by reference. Broadly speaking, PCR techniques are used to amplify a region of DNA interspersing two known DNA sequences. Collectively, the interspersing region of DNA and its flanking regions is known as an "amplicon". Two primers, a sense primer having a sequence identical or substantially identical to one end of the amplicon, and an anti-sense primer having a sequence that is the reverse complement or substantial reverse complement of the other end of the amplicon, are synthesized. The sense and anti-sense primers may be anywhere from about 5 to about 100 nucleotides in length, though other length may be possible as well. For most routine applications, the primers are typically between about 8 to about 30 nucleotides in length. PCR is usually is performed for about 20 to about 35 cycles, though more or fewer cycles may be performed depending on the specifics of the application and the desired outcome. Most commonly, each PCR cycle is carried out in three steps, often preceded by one temperature hold at the start and followed by one hold at the end.

Prior to the first cycle, during an initialization step, the PCR reaction is often heated to a temperature of 94-96° C. (or 98° C. if extremely thermostable polymerases are used), and this temperature is then held for about 1 to about 10 minutes. This first hold is employed to ensure that most of the DNA template and primers are denatured, i.e., that the DNA is melted by disrupting the hydrogen bonds between complementary bases in two DNA strands. Also, some PCR polymerases require this step for activation (i.e., a "hot-start PCR"). Following this hold, cycling begins, with one step at 94-98° C. for 20-30 seconds (denaturation step).

The denaturation is followed by an annealing step. In this step the reaction temperature is lowered so that the primers can bind to the complementary region of the denatured (i.e., single stranded) DNA template. The temperature at this step depends on the $T_m$ of the primers (see above), and is usually between 50-64° C. for 20-40 seconds.

The annealing step is followed by an extension/elongation step during which the DNA polymerase copies the DNA template, starting at the primers annealed to both of its strands. The temperature at this step depends on the DNA polymerase used. Taq polymerase has a temperature optimum of 70-74° C.; thus, in most cases, during the extension a temperature of 72° C. is used, though of course as will readily be appreciated by the practitioner, other polymerases are available and may be used as well. The final conditions of the PCR reaction will depend on a number of factors including but not limited to the identity of the polymerase employed in the procedure. The extension time depends both on the DNA polymerase used and on the length of the DNA fragment to be amplified. As a practical rule-of-thumb, at its optimum temperature, the DNA polymerase will polymerize a thousand bases in one minute. A final elongation step is frequently used after the last cycle to ensure that any remaining single-stranded DNA is completely copied. This differs from the other elongation steps only in that it is longer—typically 10-15 minutes. A final hold of 4-15° C. for an indefinite time is often employed to allow short-term storage of the reaction, especially if reactions are run overnight, and cannot be removed immediately after the cycling.

The term "real-time PCR," "quantitative PCR" or "qPCR" generally refers to modified PCR procedure in which the starting amount of target DNA, cDNA or RNA relative to other molecules in a mixture can be determined. QPCR uses fluorescent signals that are generated during the PCR procedure to calculate the amount of initial template present in a biological sample. QPCR is commonly used in the art to determine the relative expression levels of one or more genes of interest.

As used herein, the terms "PCR product", "PCR fragment" or "amplicon" generally refer to the resultant mixture of amplified DNA after two or more cycles of the PCR steps of denaturation, annealing and extension are complete. The sequence of an amplicon includes the amplified segment of DNA as well as the sequence of the primers flanking the amplified region that were employed to carry out the PCR. These terms are also meant to encompass the case where there has been amplification of one or more segments of one or more target sequences.

As used herein, the term "primer" generally refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in applications involving PCR amplification, but may alternatively, be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including annealing temperature, source of primer and the method used, all of which are readily appreciated and understood by a practitioner of ordinary skill in the art to which the present invention pertains.

As used herein, the term "oligonucleotide" (sometimes referred to simply as "oligo") generally refers to a nucleic acid molecule whose nucleic acid sequence typically comprises up to 200 nucleotides, more typically <100 nucleotides, and most typically <50 nucleotides. Oligos are commonly referred to as "N"-mers, where "N" denotes the number of bases comprising the oligo. Thus, an oligo having a sequence of 25 bases may be referred to as a 25-mer. Furthermore, oligos may be covalently modified such as, e.g., coupled to a dye, a marker, a protein, a functional group, sugars etc. Oligos may also be covalently modified (e.g., phosphorylated or dephosphorylated) at either the 5' or 3' end using a variety of chemical techniques or commercially available enzymes (e.g., kinases or phosphatases). Under the appropriate conditions (typically in aqueous solutions of appropriate temperature, pH and ionic strength) reference oligos, or sequences found within the oligos, may be made to bind to an oligo or sequences of an oligo having a sequence complementary to that of the reference oligo. It should be noted that the terms "oligonucleotide" and "polynucleotide" are both used to refer to nucleic acid molecules, the difference being that, whereas the term "oligonucleotide" is used in reference to relatively short nucleic acid molecules, the term "polynucleotide" may be used in reference to all nucleic acid molecules, irrespective of their length. Nevertheless, as will be readily appreciated by the skilled artisan, use of the terms "oligonucleotide" and "polynucleotide" in referring to "long" vs. "short" molecules may be subjective. Thus, it is to be understood that unless specified to the contrary, the terms "oligonucleotide" and "polynucleotide" may, for the purposes of the present disclosure be used interchangeably.

The term "complementary," when used in the context of a nucleic acid sequence is a well-known term of the biological arts that refers to a nucleic acid sequence that has an opposite orientation to, and is capable of forming Watson-Crick base pairs with, a reference nucleic acid sequence. Since there is only one complementary base for any of the bases found in DNA and in RNA, one can reconstruct a complementary nucleic acid sequence for any single nucleic acid sequence. The term "substantially complementary" generally means a nucleotide sequence that is complementary to at least 80%, at least 85%, at least 90%, at least 95%, or at least at least 98% of a reference nucleotide sequence. Oligonucleotides may be made using a variety of enzymatic methods, such as, PCR, primer extension, restriction digestion. Alternatively, oligonucleotides may be made using a variety of chemical techniques. Most typically, custom oligonucleotides (i.e., oligonucleotides having customer specified sequence, length and any chemical modifications) are synthesized commercially using automated DNA/RNA synthesizers, which allow for the routine synthesis of oligonucleotides up to about 200 nucleotides in length having specified or randomized sequence. Oligonucleotide synthesis and design is a highly developed art, and the properties and general uses of these molecules well known to practitioners of the biological arts. Several computer algorithms are available which aid in the design, analysis and selection of oligonucleotides and include, by way of non-limiting example, programs such as "Osprey" (described in "Osprey: a comprehensive tool employing novel methods for the design of oligonucleotides for DNA sequencing and microarrays." Gordon et al., Nucleic Acids Research 2004 32(17)); GENEWALKER™ (by CYBERGENE™ AB; http://www.cybergene.se); GeneFischer (http://bibiserv.techfak.uni-bielefeld.de/genefisher/); CLCBIO™ (http://www.cicbio.com); and The OligoFaktory (described in "OligoFaktory: a visual tool for interactive oligonucleotide design." Schretter et al., Bioinformatics. 2006 Jan. 1; 22(1):115-6) among many others. Oligonucleotide synthesis and design services are available from a number of commercial entities such as, by way of non-limiting example only, INVITROGEN®, BIONEER® INC., BIOSEARCH TECHNOLOGIES®, EXIQON®, IDAHO TECHNOL- OGY® INC., LC SCIENCES®, MIDLAND CERTIFIED REAGENT COMPANY®, SBS GENETECH®, THERMO SCIENTIFIC®, YORKSHIRE BIOSCIENCE® LTD, ALPHA DNA®, MICROSYNTH® AG, BIOSERVE®, BIO-SYNTHESIS®, EUROGENTEC EXPRESSON BIO-SYSTEMS® LTD., FAVORGEN BIOTECH® CORP., IBA® GMBH, ILLUMINA® MWG, BIOTECH OLIGO FACTORY®, OLIGOS ETC. INC., OPERON BIOTECHNOLOGIES® INC., PROLIGO®, RETROGEN®, ROCKLAND IMMUNOCHEMICALS® INC., and SEQWRIGHT®.

As used herein, the term "recombinant," when used in reference to a polynucleotide or a protein, generally refers to a polynucleotide or a polypeptide molecule that is produced using genetic engineering techniques and that is distinct from a naturally occurring nucleic acid or polypeptide molecule. Recombinant DNA (sometimes represented as "rDNA") is an artificial DNA sequence resulting from the combining of two other DNA sequences in a plasmid/vector. The term recombinant DNA refers to a new combination of DNA molecules that are not found together naturally. Although processes such as crossing over (genetic recombination) technically produce recombinant DNA, the term is generally reserved for DNA produced by joining molecules derived from different biological sources.

The term "portion", as used herein, in the context of a molecule, such as a polypeptide or of a polynucleotide (as in "a portion of a given polypeptide/polynucleotide") generally refers to fragments of that molecule. The fragments may range in size from three amino acid or nucleotide residues to the entire molecule minus one amino acid or nucleotide. Thus, for example, a polypeptide "comprising at least a portion of the polypeptide sequence" encompasses the polypeptide defined by the sequence, and fragments thereof, including but not limited to the entire polypeptide minus one amino acid.

As used herein, the term "Systematic Evolution of Ligands by Exponential Enrichment" or "SELEX" generally refers to a combinatorial technique used in molecular biological for producing oligonucleotides of either single-stranded DNA or RNA ligands that specifically bind to a target molecule. The selected sequences are referred to as aptamers. Very broadly, the process begins with the synthesis of a very large oligonucleotide library consisting of randomly generated sequences of fixed length flanked by constant 5' and 3' ends that serve as sequences suitable for primer binding and amplification. For a randomly generated region of length n, the number of possible sequences in the library is $4^n$. The sequences in the library are exposed to the target molecule—which may be a protein or small organic or inorganic compound—and those that do not bind the target even weakly are removed, usually by affinity chromatography. The bound sequences are isolated and amplified by PCR to prepare for subsequent rounds of selection in which the stringency of the elution conditions is increased (i.e., by changing incubation temperature, ionic concentration, or by adding a weak denaturant) to identify the highest-affinity sequences. The technique has been used to evolve aptamers of extremely high binding affinity to a variety of target molecules, including small molecules such as ATP and adenosine as well as proteins such as prions and vascular endothelial growth factor (VEGF). Clinical uses of the technique are suggested by aptamers that bind tumor markers. For example, clinical trials are underway for a VEGF-binding aptamer trade-named Macugen in treating macular degeneration. One caution advanced in relation to the method emphasizes that selection for extremely high, sub-nanomolar binding affinities may not in fact improve specificity for the target molecule. Off-target binding to related molecules could have significant clinical effects (see, e.g., Dieckmann et al., (1996). Solution structure of an ATP-binding RNA aptamer reveals a novel fold. *RNA* 2(7):628-40; Huizenga et al. (1995). A DNA aptamer that binds adenosine and ATP. *Biochemistry* 34(2):656-65; Mercey et al., (2006) Fast, reversible interaction of prion protein with RNA aptamers containing specific sequence patterns. *Arch Virol* 151(11):2197-214; Burke D H, Gold L. (1997). RNA aptamers to the adenosine moiety of S-adenosyl methionine: structural inferences from variations on a theme and the reproducibility of SELEX. *Nucleic Acids Res* 25(10): 2020-4; Ulrich et al., (2006). DNA and RNA aptamers: from tools for basic research towards therapeutic applications. *Comb Chem High Throughput Screen* 9(8):619-32); Ferreira et al., (2006). DNA aptamers that bind to MUC1 tumour marker: design and characterization of MUC1-binding single-stranded DNA aptamers. *Tumour Biol* 27(6):289-301; Vavvas et al., (2006). Pegaptanib (Macugen): treating neovascular age-related macular degeneration and current role in clinical practice. *Ophthalmol Clin North Am.* 19(3):353-60; Carothers et al., (2006). Aptamers selected for higher-affinity binding are not more specific for the target ligand. *J Am Chem Soc* 128(24):7929-37). Methods and variations thereof for performing SELEX are also described in detail in U.S. Pat. Nos. 7,176,295; 6,855,496; 6,730,482; 6,706,482; 6,613,526; 6,506,887; 6,465,189; 6,387,620; 6,376,474; 6,376,190; 6,300,074; 6,291,184; 6,261,774; 6,114,120; 6,083,696; 6,030,776; 6,013,443; 6,001,577; 5,998,142; 5,962,219; 5,864,026; 5,861,254; 5,858,660; 5,789,160; 5,789,157; 5,773,598; 5,763,595; 5,763,566; 5,763,177; 5,723,592; 5,723,289; 5,712,375; 5,705,337; 5,683,867; 5,637,459; and 5,567,588, as well as U.S. Patent Application Publication Nos. 2006/0088877; 2005/0136474; 2004//0132067; 20030099945; 2003/0087301; 2003/0077646; 2003/0044818; 2003/0027781; 2003/0003461; 2002/0106652; 2002/0102599. The text of the foregoing references and patent publications are hereby expressly incorporated by reference in their entirety as though fully set forth herein.

As used herein, the term "separating" when used in the context of target molecule/aptamer selection methods, generally means separation of oligonucleotide/target complexes, preferably DNA/protein complexes, from the surrounding pool of unbound oligonucleotides. This may be accomplished using one or more physical separation means, such as, by way of various non-limiting examples, affinity chromatography (e.g., biotin/avidin, antibody affinity, metal ion affinity chromatography, or using a target molecule-fusion protein such as glutathione S-transferase, Maltose Binding Protein, or the like); filtration; magnetic bead separation, centrifugation, chemical extraction, or any of the methods described in the aforementioned patents and incorporated herein, or by enzymatic means (such as, e.g., enzymatic hydrolysis of unbound oligonucleotides).

The terms "5'" and "3'," when used in the context of a reference nucleic acid molecule, are generally used to indicate the directionality of the nucleic acid molecule. The chemical convention of naming carbon atoms in the nucleotide sugar-ring numerically gives rise to a 3' end and a 5' end. The relative positions of structures along a strand of nucleic acid, including genes, transcription factors, and polymerases are usually noted as being either upstream (towards the 5' end) or downstream (towards the 3' end). The importance of having this type of naming convention is easily demonstrated by the fact that nucleic acids can only be synthesized in vivo in a 5' to 3' direction, as the polymerase used to construct new strands must attach a new nucleotide to the 3' hydroxyl (—OH) group via a phosphodiester bond. For this and other reasons, DNA and RNA sequences are conventionally written starting from the 5' end of the molecule, and proceeding to the 3' end. Thus, the reference sequence GGATTC, for example, is the convention used to represent a DNA molecule having the structure 5'OH-GGATTC-3'OH. Conversely, it's reverse complement (i.e., a sequence that would, under the appropriate conditions, form Watson-Crick base pairing with this reference sequence is GAATCC, and represents the structure 5'OH-GAATCC-3'OH.

As used herein, the term "endonuclease" generally refers to a class of enzymes that cleave phosphodiester bonds within a polynucleotide chain. Restriction endonucleases (restriction enzymes) cleave DNA at or near specific recognition sites (sequences). Non-specific endonucleases, on the other hand, cleave DNA or RNA into mono-, di-, tri-, or oligonucleotide products. Exemplary non-specific endonucleases include DNase I, S1 Nuclease, Nuclease Bal31 (which is also an exonuclease), Mung-bean nuclease, T7 Endonuclease I.

As used herein, the term "exonuclease" generally refers to a class of enzymes that cleave nucleotides one at a time from an end of a polynucleotide chain. These enzymes hydrolyze phosphodiester bonds from either the 3' or 5' terminus of polynucleotide molecules. Exonucleases that hydrolyze nucleotides from the 5' end of a nucleic acid molecule may generally be referred to as a 5'→3' exonucleases. Examples of 5'→3' exonucleases include, by way of illustration only, λ-exonuclease, T7 Exonuclease, and RecJ. Exonucleases that hydrolyze nucleotides from the 3' end of a nucleic acid molecule may generally be referred to as a 5'→3' exonucleases. Illustrative examples of 3'→5' exonucleases include Exonuclease I, Exonuclease III, and Exonuclease T. Nuclease Bal31, which also functions as an endonuclease, is both a 5'→3' exonuclease and a exonuclease. In some embodiments, exonucleases may be employed in which only functions exists, and other functions have been experimentally or naturally abolished. One non-limiting example of such a molecule is Klenow(5'→3' exo) (which may also be written as Klenow (Asp$^{335}$; Glu$^{357}$; 5'→3' exo$^-$), in which the 5'→3' exonuclease activity has been abolished, but the 3'→5' exonuclease activity of the enzyme is retained. Of course, for the purposes of the present disclosure, it will be readily appreciated by a practioner of ordinary skill in the art that additional endonucleases and exonucleases exist which, though not listed above, are suitable for use within the context of the present invention, without departing from the sprint and scope thereof, and that failure to list them above in no way precludes their use in one or more of the foregoing described embodiments.

As used herein, the term "secondary structure," when used in the context of a reference nucleic acid molecule, generally refers to the general three-dimensional form of local segments of nucleic acids (DNA/RNA). It does not, however, describe specific atomic positions in three-dimensional space, which are considered to be tertiary structure. Secondary structure is formally defined by the hydrogen bonds of the biopolymer, as observed in an atomic-resolution structure. In nucleic acids, the secondary structure is defined by the hydrogen bonding between the nitrogenous bases. The term may also be applied to describe various aspects of protein structure, however such an application is beyond the scope of the present disclosure and will thus not be considered further. secondary structure occurs most notably in single-stranded nucleic acid (RNA and DNA) molecules. Secondary structure in nucleic acids may generally be divided into two broad categories: helices and various kinds of loops. Helices occur when two complementary or substantially complementary sequences that are present in the same nucleic acid molecule anneal (either by traditional Watson-Crick base pairing or, in the case of RNA, also by Hoogsteen base pairing). Typically, such helices form when a nucleic acid molecule has at least two complementary or substantially complementary sequences arranged either as everted repeats or as inverted repeats. Helices that form within the same nucleic acid molecule may also be said to be forming "intramolecular" base pairing. Thus, intramolecular base pairing may be differentiated from intermolecular base pairing, which occurs between two individual and separate complementary or substantially complementary nucleic acid molecules. The various types or unpaired loops that comprise secondary structures are generally found interspresed between helices. An example of a typical secondary structure is the stem-loop, in which a base-paired helix ends in an unpaired nucleic acid loop. Internal loops (short series of unpaired bases in a longer paired helix) and bulges (regions in which one strand of a helix has "extra" inserted bases with no counterparts in the opposite strand) are also frequent. The present invention utilizes predictable intramolecular secondary structure to subject unbound aptamers to nuclease digestive deslection.

As used herein, the terms "nucleic acid ligand library," "nucleic acid library," "oligo library," "polynucleotide library," or the like, generally refer to a mixture of nucleic acid molecules having variable sequence from which to select an aptamer to a specific target molecule. The variable region will, for the purposes of the present disclosure, unless otherwise indicated, encompass the population of oligonucleotides having the sequence 5'-$N_x$-'3, where each N is independently A, G, C, or T (where T is replaced by U in the case where RNA is employed), and where x is an integer corresponding to the number of bases in the polynucleotide molecules of the library. Thus, for a polynucleotide library having whose constituent polynucleotide molecules have a length of about 1 kB, x is about 1000. In the case where the polynucleotide library comprises oligonucleotides, x will typically range from about 5 up to about 200, or up to about 150, or up to about 100, or up to about 50. In some non-limiting embodiments, x is between about 12 to about 25, or between about 15 to about 18. Thus, in this latter case there will exist in such a library between about $4^{15}$ to about $4^{18}$ unique oligonucleotide sequences. The constituent molecules of a nucleic acid ligand library may be naturally occurring nucleic acids or fragments thereof (such as is found, e.g., in a cDNA or EST library), chemically synthesized nucleic acids, enzymatically synthesized nucleic acids or nucleic acids made using any combination of the aforementioned techniques. In a subset of embodiments, each nucleic acid molecule in the library may include one or more fixed (e.g., known) nucleotide sequences 5' to, 3' to, or flanking, the variable region for the purpose of facilitating the enrichment and identification of target aptamers (such as by using PCR, affinity chromatography, or any similar methods used to purify or enrich target nucleic acids). In some embodiments, such fixed nucleotide sequences may be referred to as "adapters" or alternatively "tags." The sequence of the adapters used in the present description is entirely arbitrarily, chosen only for the purposes of clarifying the invention. It will be readily understood by the skilled artisan that other adapters may also be used, without departing from the spirit and scope of the embodiments set forth herein, the only limitation being that they are selected to generally confer secondary structure due to complementarities of the termini. One general exemplary adapter inclusive sequence that may be used in accordance with the present embodiments is, by way of a first non-limiting example, the sequence 5'-$Z_x$—$N_x$—$Z'_x$-3', where N is A, G, C, T or, in the case of RNA, U, and where x is an integer from about 5 to about 100, or larger, where Z and Z' is A, G, C, T or, in the case of RNA, U, and where x is an integer from about 5 to about 100, or larger, and where 4 and Z'$_x$ are complementary, or substantially complementary, to each other, thus forming secondary structure at the termini in physiological solution. One exemplary adapter inclusive sequence that may be used in accordance with the present embodiments is, by way of a first non-limiting example, the sequence 5'-TTTGGGGGGGGTTTTTTTTGGG-N$_x$-CCCAAAAAAAACCCCCCCCAAA-3', where N is A, T, G, or C. where N is A, G, C, T or, in the case of RNA, U, where x is an integer from about 5 to about 100, or larger, where the sequence 5% TTTGGGGGGGGTTTTTTTTGGG-3' (SEQ ID NO:1) is an example of the 4 structure, and where the sequence 5'-CCCAAAAAAAACCCCCCCCAAA-3' (SEQ ID NO:2) is an example of the Z'$_x$ structure (or vice versa). Another exemplary adapter inclusive sequence that may be used in accordance with the present embodiments is, by way of a first non-limiting example, the sequence 5'-TTTGGGGGGGATCCTTTTTGGG-N$_x$—CCCAAAAAGGATCCCCCCCAAA-3', where N is A, T, G, or C or, in the case of RNA, U, where x is an integer from about 5 to about 100, or larger, where the sequence 5'-TTTGGGGGGGATCCTTTTTGGG-3' (SEQ ID NO:3), is another example of the 4 structure, and where the sequence 5'-CCCAAAAAGGATCCCCCCCAAA-3' (SEQ ID NO:4) is an example of the Z'$_x$ structure (or vice versa), and where the complementary adapter sequences form a secondary structure which includes a BamHI restriction enzyme site. This is a non-limiting example, as other restriction sites could also be used to make the secondary structure vulnerable to nuclease digestive de-selection. Another exemplary adapter sequence that may be used in accordance with the present embodiments is, by way of a second non-limiting example, the sequence 5'-N$_x$-3', where N is A, G, C, T or, in the case of RNA, U, and where x is an integer from about 5 to about 100, or larger. In some embodiments, x may be from about 5 to about 50, or from 5 to about 100, or larger. An adapter may be synthesized as part of the oligonucleotide, or may be added to the oligonucleotide after the synthesis thereof. An oligonucleotide may be added, for example, by ligating one or more adapter sequences to the 5' or the 3' end of an oligonucleotide. Alternatively a poly-T adapter, a poly-A adapter, a poly-G adapter, a poly-C adapter, or a poly-U adapter may be added to the 3' end of the nucleic acid oligonucleotides comprising the library using an enzyme such as terminal transferase (TdT) as a template independent polymerase that catalyzes the addition of deoxynucleotides to the 3' hydroxyl terminus of DNA molecules.

The term "amplifying," as used herein, generally refers to the duplication (by enzymatic means) of an oligonucleotide using a nucleotide polymerase enzyme such as DNA or RNA polymerase. Where amplification employs repetitive cycles of duplication such as using the "polymerase chain reaction," the polymerase is a heat stable polymerase such as the DNA polymerase of *Thermophilus aquaticus* (Taq).

The term "knockdown" is used herein to describe one process by which target-specific aptamers may be enriched from an oligonucleotide library. The term is meant to refer to the ability of target-bound aptamers to resist hydrolysis by various nucleases. Unbound oligonucleotides, on the other hand, are susceptible to enzymatic hydrolysis and their effective concentration is "knocked-down" in the presence thereof. The term, in the present context, is not to be confused with the unrelated process of RNA-interference (RNAi), which is sometimes also referred to as RNA-"knockdown." The terms "exclusion" and "subtraction" may also be used herein with the same meaning as knockdown.

"Contacting" in the context of target selection, generally refers to incubating an oligonucleotide library with target molecules. By "target molecule" is meant any molecule to which a specific aptamer selection is desired.

The term "target molecule" generally refers to any compound of interest for which an aptamer is desired. A target molecule may be a protein, a peptide (i.e., a 'small' protein), a carbohydrate, a polysaccharide, a glycoprotein, an hormone, a receptor, an antigen, an antibody, a virus, a prion, a substrate, a metabolite, a transition state analog, a cofactor, an inhibitor, a drug, a dye, a nutrient, a growth factor, an organic compound, or an inorganic compound, without limitation.

The term "binding buffer," when used in the context of binding a target molecule to an aptamer, generally refers to any suitable aqueous medium that enables or permits the interaction between a target molecule and an aptamer to occur. The composition of a binding buffer is not limited to any one particular formulation or component. On the contrary, the composition of a binding buffer may be tailored to a particular application or to a particular setting. In some embodiments, a binding buffer may be a physiologically hypertonic aqueous solution. In some embodiments, a binding buffer may be a physiologically hypotonic aqueous solution. In some embodiments, a binding buffer may be a physiologically isotonic aqueous solution. In one non-limiting embodiment, a binding buffer may be, e.g., a phosphate buffered solution. In an embodiment, a binding buffer may be, e.g., whole blood, fractionated blood, whole serum, or blood plasma. In one non-limiting set of embodiments, a binding buffer may typically comprise, e.g., about 1 mM to about 100 mM Tris, from about 10 mM to about 500 mM NaCl, from about 0.5 mM to about 50 mM KCl, from about 0.1 mM to about 10 mM $CaCl_2$. The pH of a binding buffer will generally be in the physiological range, e.g., preferably about 6-8, more preferably about 6.5-7.5, and most preferably about 7.0-7.5. Optionally, a binding buffer may include, for example, a carrier nucleic acid (e.g., from about 0.1 mg/ml to about 100 mg/ml tRNA) to prevent adsorption of library oligos to the wall of any vessel in which a screening procedure is being conducted. One non-limiting example of a typical binding buffer formulation suitable for the systems and methods described herein is 20 mM Tris; 140 mM NaCl; 5 mM KCl, and 1 mM $CaCl_2$ and 10 mg/ml tRNA. The final components of a binding buffer ultimately vary, depending on a number of variables including but not limited to the identity and nature of the molecules involved, the equilibrium of the solution, and the relative binding affinity of the molecular association (typically denoted by a binding constant $K_d$). Secondary factors such as, e.g., the temperature of the system may also affect the binding conditions and thus selection of the constituents of a binding buffer. Optionally, agents such as ionic or non-ionic detergents, or other chaotropes, may be included in a binding buffer to influence the binding between a target and an aptamer (i.e., to insure that only high affinity aptamers are selected).

As used herein, the term "gene" generally refers to a functional unit of a polynucleotide molecule, typically a DNA molecule, which controls or influences one or more discreet, heritable and/or transferable phenotypes. Usually, though not exclusively, a gene corresponds to a single polypeptide or RNA, or isoforms thereof. A gene may designate an entire functional unit such as is found in the genome, including but not limited to coding regions (e.g. open reading frames), non-coding regulatory regions (e.g. promoters, enhancers, termination and polyadenylation signals, and the like) and introns. Alternatively, a gene may designate only portions or fragments thereof, such as, for example, a cDNA. A gene may be either chromosomal or extra-chromosomal. Furthermore, shuttle vectors are typically used to transfer isolated polynucleotides between cells of the same or different species. Viral vectors are typically packaged in viral coat proteins and are used for high efficiency transfection and/or expression of isolated polynucleotides in cells. In some cases, viral vectors will integrate into a host cell genome and become a transgene. Bacteriophage vectors are often used during gene cloning procedures (e.g., isolation and enrichment of polynucleotides). An ordinary practitioner of the art would readily appreciate however, that the aforementioned vector classifications are not mutually exclusive and that the placement of a vector in one of the aforementioned classifications does not preclude its placement in additional classifications. Rather, many vectors may be placed in a plurality of the aforementioned vector classifications. For example, subsets of expression vectors are also viral vectors, and subsets of expression vectors are also shuttle vectors. Additionally, many bacteriophage vectors are also cloning, shuttle and expression vectors. An "expression vector" is a nucleic acid construct, typically generated using recombinant DNA techniques, which contains a series of specified nucleic acid elements that permit transcription of a particular nucleic acid in a host cell. An expression vector may also optionally be adapted to allow for its integration and/or replication in a host cell. An expression vector may be part of a plasmid, a virus, or a nucleic acid fragment, of viral or non-viral origin. Typically, the expression vector includes an "expression cassette," into which may be inserted, using recombinant DNA techniques, an isolated polynucleotide that is to be expressed in a host cell. The isolated polynucleotide is operably-linked to one or more appropriate nucleic acid sequences that are necessary for or that augment the expression of the isolated polynucleotide in a particular host cell or organism. Nucleic acid sequences necessary for expression in prokaryotes usually include a promoter, an optional operator, and a ribosome binding site, often along with other sequences. Nucleic acid sequences necessary for the expression of a protein from an expression vector in eukaryotic cells include at least one promoter, termination and polyadenylation signals, and one or more optional enhancers.

General Description

Disclosed herein are novel methods of selecting aptamers that bind to a target molecule. Aptamers selected in accordance with the presently described embodiments may be selected in as few as 1 cycle of selection, or up to several hundred cycles of selection. Typically, aptamers selected in accordance with the presently described embodiments may be selected in up to about 15 cycles of selection. In some embodiments, aptamers selected in accordance with the presently described embodiments may be selected in about 1 to about 5 cycles, or in about 1 to about 3 cycles.

In an embodiment, a first cycle of aptamer selection may be performed at a first temperature, e.g., room temperature (about 20° C. to about 25° C.). The aptamers selected at the first temperature may then be subjected to a second round of selection. In an embodiment, the second round of selection may be carried out at a second temperature. The second temperature may be higher than, lower than, or substantially equal to the first temperature used to select the aptamers. Without being bound to any one particular theory or mechanism of action, and in full appreciation that other mechanisms of action not presently contemplated may be operative, increasing the temperature at which the aptamer is selected may increase the stringency of the screen for aptamers that bind to the target molecule. In an embodiment, a temperature at which a second round of selection may be performed may be in the range of, e.g., 27° C. to about 34° C.

The aptamers selected at the second temperature may then be subjected to a third cycle of selection. In an embodiment, the third cycle of selection may be carried out at a third temperature. The third temperature may be higher than, lower than, or substantially equal to the first or the second temperature used to select the aptamers. In an embodiment, the third temperature at which aptamers are selected may be substantially body temperature (i.e., around 37° C.). Again, without being bound to any one particular theory or mechanism, selecting aptamers at body temperature may select those aptamers that interact with the target molecule more efficiently and with greater affinity. Such aptamers are generally expected to have greater therapeutic utility in vivo. This may occur, for example because differences in the secondary structure of an aptamer, or in the tertiary structure of a protein target molecule, at body temperature enable them to interact with each more efficiently than they would at lower temperature.

It is desirable to provide an improvement over existing methods for selecting aptamers (e.g., by SELEX), since the method of isolating aptamers from unbound oligonucleotides might not require a step in which aptamers are physically separated from the oligonucleotide pool (such as, e.g., filtration, magnetic separation etc.). In this way, it is generally believed that the present invention may allow for the identification of weaker aptamers, i.e., those whose binding with the target molecule has a relatively low equilibrium constant, $K_{eq}$, and thus would otherwise be discarded.

An advantage of the method and system disclosed herein for selecting aptamers is that method may not require elaborate and expensive instrumentation. In contrast to methods such as SELEX, selection of aptamers in accordance with the presently described embodiments may be performed utilizing only a thermocyler and a benchtop centrifuge or vacuum manifold, all of which are standard equipment in most life science labs.

An advantage of the method and system disclosed herein for selecting aptamers is that method digests the flanking sequence of many unbound aptamer candidates with nucleases so that they are not amplified during enrichment cycling. Without this treatment, many more unwanted aptamer candidates are brought forward during physical separation step and are amplified during SELEX cycling, contributing to the high number of cycles currently required by SELEX. The proposed method should reduce the number of cycles required and may even obviate the need for physical separation of bound and unbound aptamers between cycles. Most importantly, the proposed method should also increase the chance that the selected "aptamers" are indeed aptamers for the target, thereby saving much wasted time and expense. Too often the SELEX process produces aptamer candidates that don't actually bind to the intended target, Disclosed herein is a method that utilizes a "two-pronged" strategy to enrich and amplify aptamers. For example, in an embodiment performed in accordance with the following description, aptamers may first be selected from an oligonucleotide library by subjecting oligonucleotide molecules that are not bound to the target to enzymatic hydrolysis (knockdown). Bound oligonucleotides are then subject to PCR amplification and are then either identified and sequenced, or are subject to further rounds of enrichment and selection.

Disclosed herein is an efficient means of selecting aptamers under substantially physiological conditions (e.g., selecting in blood matrix, or selecting in blood matrix in conjunction with the physical separation tactics of SELEX).

Disclosed herein is a method that may be employed in conjunction with SELEX.

Disclosed herein is a method that may be employed to introduce into aptamers a susceptibility to digestion by endonucleases (including restriction enzymes) and exonucleases by utilizing sequences that predict complementary, secondary structure involving the termini.

Still further embodiments concern kits suitable for the purpose of performing a screen for aptamers that bind to a molecule of interest. The kits include, in at least a first suitable container, a suitable oligonucleotide library, one or more endonucleases (including restriction enzymes), and one or more exonucleases, in conjunction with instructions for use in performing a screen for aptamers that bind to a molecule of interest. A kit may optionally further contain one or more appropriate binding buffers, and/or one or more buffers suitable to enable activity of the provided nucleases. The kit may further contain one or more reagents, including suitable buffer, enzymes and primers, for amplifying selected aptamers by PCR.

DNA aptamers can be used in certain detection, diagnostic and identification systems, including for biological and chemical threat agents, as well as for neutralization and therapeutics. There is a need for new technologies to select and manufacture DNA aptamers which (1) address the mass action problem of weak binders competing out strong binders, (2) can save both time and expense in the biosynthetic methods employed in the Systemic Evolution of Ligands by Exponential enrichment (SELEX) method, and (3) can be miniaturized and packaged onto user friendly instruments. A method is therefore needed which DNA may rapidly and cost-effectively select aptamers with high binding affinity and high specificity, after only one or at most a few rounds of selection.

To address this technical hurdle the Lariat Aptamer technology, which is a significant improvement of a method known as "Knockdown Nuclease Protected Aptamer Selection and Acquisition" (KN-PASA), previously described in U.S. Provisional Patent Application No. 60/903,243 and in U.S. patent application Ser. No. 12/033,522, which lends foundation to the present disclosure, is disclosed herein.

Toward that aim, it is useful to review the KN-PASA technology, including its limitations. In the KN-PASA technology, the resistance to hydrolysis by various nucleases of a target-bound aptamer is exploited as a method to separate target-bound aptamers from unbound oligonucleotides. The same is true of the Lariat Aptamer approach only there is a great advantage in knowing that the termini form a complementary, secondary structure.

FIG. 1, originally drawn to depict KN-PASA is also illustrative of Lariat Aptamer Selection, except that the sequence of the nucleotide library differs. The first step in performing Lariat Aptamer selection may include incubating a target molecule of interest with nucleic acid ligand library under conditions (e.g., at room temperature or higher) that would allow binding of the target molecule to one or more aptamers present in the nucleic acid ligand library. Typically the target molecule will be at least partially purified and dissolved in an appropriate aqueous medium, such as an appropriate binding buffer. Thus, in FIG. 1A, a target molecule (e.g., thrombin) is contacted with a nucleotide candidate library. In the non-limiting case shown in FIG. 1A, thrombin is used, however, it is to be understood that the use of thrombin herein is for the purpose of illustration only and is non-limiting for the present methods. Except for the sequence, FIG. 1A may also represent the initial step of the Lariat Aptamer approach. The library depicted FIG. 1A includes a variable region having the sequence 5'-$N_{20-50}$-3' having the 5' adapter sequence shown in FIG. 1A attached to the 5' end thereof. By contrast, as FIG. 2 shows, the Lariat Aptamer approach has both a 5' adapter ('5-$Z_x$—) and a 3' adapter (—$Z'_x$-3') in the starting material and the adapters are complementary to one another, forming secondary structure at the termini and this is a major advantage.

Turning now to FIG. 1B, it can be seen that the incubation step could result in a variety of products including but not limited to a) unbound single-stranded oligos, b) unbound oligos having secondary structure with, or without, involvement of the termini, c) unbound target molecule, and d) aptamer-bound target. The same is true for the Lariat Aptamer approach.

The goal of the Lariat Aptamer technique is to subtract (i.e., knock-down) the unbound single-stranded oligonucleotides and unbound oligonucleotides having secondary structure by digesting them with nuclease so that they are not amplifiable by PCR when using primers targeting the initial termini. In an embodiment, separation of the unbound single-stranded oligos and unbound oligos having secondary structure from target-bound aptamers may be accomplished by adding one or more nucleases to the mixture resulting in the step depicted in FIG. 1B, thereby enriching target bound aptamers. In one embodiment, enrichment of target-bound aptamers may be accomplished by adding to the mixture depicted in FIG. 1B, one or more endonucleases, one or more exonucleases, or one or more endonucleases in combination with one or more exonucleases. This is also true of the Lariat Aptamer approach. Nucleases suitable for use in the Lariat Aptamer embodiments may include, though are not limited to S1 Nuclease, DNAses, RNAses, Type-II Restriction Enzymes (for example Bam-HI), Exonuclease I, Exonuclease III, and Exonuclease T, T7 Exonuclease, Klenow (5'→3' exo$^-$), Lambda Exonuclease, Mung Bean Nuclease, Microccocal Nuclease, RecJf, and Nuclease BAL-31. As is depicted in FIG. 1C, target-bound aptamers are resistant to nuclease digestion and are thereby enriched in solution.

In a next step, selected or enriched aptamers are liberated from the target molecule. This may be accomplished using any method of disrupting intermolecular hydrogen bonding, such as by, e.g., subjecting the sample containing aptamer bound target to denaturing conditions (e.g., heat denaturation, addition of detergents or chaotropes, phenol extraction, and the like). In the case of heat denaturation, the sample may be subjected to up to 100° C. for 10 seconds to 10 min, or longer to inactivate the nucleases. Optionally the enriched aptamers may be subjected to one or more rounds of selection under more stringent, conditions (lower ionic strength, higher temperature etc.), and subjected to further nuclease degradation in one or more additional enrichment cycles. For example, in an embodiment, second or subsequent rounds of selection may be conducted at 30° C. rather than 22° C.

Unlike in the KN-PASA technique, the tailing step using Terminal Transferase shown in FIG. 1D may not be required by the Lariat Aptamer approach, since it already has a 3' terminus of known sequence (—$Z'_x$-3'). The two-pronged enrichment strategy is accomplished by alternating nuclease knockdown of non-binders with PCR amplification of binders (see FIG. 1). Prior to subjecting the selected aptamer candidates to further enrichment cycles, the double-stranded amplicons comprising the aptamer candidate pool may first be denatured to single-stranded molecules. After the final round of aptamer selection, the double-stranded aptamer candidate may be sequenced, and the strand to which the target molecule binds may be identified by preparing single-stranded oligonucleotides corresponding to each strand, and independently testing their ability to bind to the target molecule.

The aptamers that are selected are then further characterized for binding affinity and specificity. Because of the relative ease and adaptability of the Lariat Aptamer selection methods, the use thereof in conjunction with other SELEX protocols is equally contemplated.

Because KN-PASA technology employs nucleases to knockdown potential aptamers without a priori knowledge of sequence and, therefore, structure, it is not as powerful as the Lariat Aptamer Technology disclosed herein. In contrast to the originally proposed KN-PASA technology, the Lariat Aptamer technology takes advantage of predictable secondary structure. The secondary structure makes unbound aptamer candidates vulnerable to nuclease digestion thereby excluding them from selection and enriching bound molecules. In the Lariat Aptamer approach, a priori knowledge of structure provides a huge advantage over the KN-PASA. Turning to FIG. 2, a Lariat Aptamer Nucleotide Library is shown forming an invariant terminal secondary structure (the handle) and a variable intervening region (the Loop or Key). In the non-limiting case shown in FIG. 2, the sequence 5'-TTTGGGGGGGGTTTTTTTGGG-$N_x$-CCCAAAAAAAACCCCCCCAAA-3" [which contains 5'-TTTGGGGGGGGTTTTTTTGGG-3' (SEQ ID NO:1) and 5'-CCCAAAAAAAACCCCCCCAAA-3' (SEQ ID NO:2)] is used, however, it is to be understood that the use of the sequence herein is for the purpose of illustrating an exonuclease-susceptible handle only and is non-limiting for the present methods. In other embodiments, endonuclease sites (including type II restriction enzyme sites) are formed in the secondary structure and digestible by restriction enzymes.

Lariat Aptamer technology is equally applicable to any sequence forming complementary termini, or handle, without limitation. It is anticipated that some apatmer candidates may not form complementary termini, despite a sequence that would predict such a structure. When unbound, these structures can be subtracted by utilizing Exonuclease I, DNase I, other single strand digesting nucleases.

Each incubation/nuclease digestion cycle enriches for target binding aptamers and excludes non-binders. The cycling is repeated until the complexity is reduced to the point that binding aptamers are selected.

EXAMPLES

Having now described the invention, the same will be more readily understood through reference to the following example(s), which are provided by way of illustration, and are not intended to be limiting of the present invention.

Example 1

One general example of the starting material for a nucleotide library is the sequence 5'-$Z_x$—$N_x$—$Z'_x$-3', where $N_x$ (which forms the Loop or Key) is A, G, C, T or, in the case of RNA, U, and where x is an integer from about 5 to about 100, or larger, where Z and Z' is A, G, C, T or, in the case of RNA, U, and where x is an integer from about 5 to about 100, or larger, and where $Z_x$ and $Z'_x$ (which form the Handle) are complementary, or substantially complementary, to each other, thus forming secondary structure at the termini in physiological solution. One more specific example of the above form is the sequence 5'-TTTGGGGGGGGTTTTTTTGGG-$N_x$-CCCAAAAAAAACCCCCCCAAA-3', where N is A, T, G, or C. where N is A, G, C, T or, in the case of RNA, U, where x is an integer from about 5 to about 100, or larger, where the sequence 5'-TTTGGGGGGGGTTTTTTTGGG-3' (SEQ ID NO:1) is an example of the 4 structure, and where the sequence 5'-CCCAAAAAAAACCCCCCCAAA-3' (SEQ ID NO:2) is an example of the $Z'_x$ structure (or vice versa). This sequence is predicted to form secondary structure as shown in FIG. 2. Those nucleotide library molecules that are not bound to their target are susceptible to nuclease digestion, for example by Exonuclease III. Once digested, they are no longer amplifiable by the PCR primer 5'-TTTGGGGGGGGTTTTTTTGGG-3' (SEQ ID NO:1) and are therefore excluded from selection. By contrast, those nucleotide library molecules that are bound to their target are not as susceptible to exonuclease digestion, due to steric hindrance. Accordingly, they survive disproportionately and are amplifiable by the PCR primer 5'-TTTGGGGGGGGTTTTTTTGGG-3' (SEQ ID NO:1) and remain in the selection process.

Example 2

Another specific example of the 5'-$Z_x$—$N_x$-$Z'_x$-3' form is the sequence 5'-TTTGGGGGGGATCCTTTTTGGG-$N_x$-CCCAAAAAGGATCCCCCCCAAA-3', where N is A, T, G, or C. where N is A, G, C, T or, in the case of RNA, U, where x is an integer from about 5 to about 100, or larger, where the sequence 5'-TTTGGGGGGGATCCTTTTTGGG-3' (SEQ ID NO:3) is an example of the 4 structure, and where the sequence 5'-CCCAAAAAGGATCCCCCCCAAA-3' (SEQ ID NO:4) is an example of the $Z'_x$ structure (or vice versa), which includes a BamHI restriction enzyme site. This is a non-limiting example, as any type II restriction site might be employed to make the secondary structure vulnerable to digestive de-selection with restriction enzymes. This sequence is predicted to form secondary structure similar to that shown in FIG. 2. Those nucleotide library molecules that are not bound to their target are susceptible to nuclease digestion, for example by BamHI restriction enzyme and/or by Exonuclease III. Once digested, they are no longer amplifiable by the PCR primer 5'-TTTGGGGGGGATC-CTTTTTGGG-3' (SEQ ID NO:3), or similar primers, and are therefore excluded from selection. By contrast, those nucleotide library molecules that are bound to their target are not susceptible to digestion by either BamHI or Exonuclease III, due to steric hindrance. Accordingly, they are amplifiable by the PCR primer 5'-TTTGGGGGGGATCCTTTTTGGG-3' (SEQ ID NO:3) and proceed through the selection process.

Example 3

Exonuclease I may, in some embodiments, be used to hydrolyze unbound oligos lacking secondary structure at the 3' end (Lehman and Nussbaum, 1964; Goldmark and Linn, 1972; Rosamond et al., 1979). One Unit of Exonuclease I is defined as the amount of enzyme that will catalyze the release of $6 \times 10^{15}$ bases in 30 minutes at 37° C. A first embodiment may begin with about 1.0 nmol of oligonucleotide library. The number of bases this represents can be calculated as follows: $((6 \times 10^{23}$ molecules/mole$) \times (10^9$ moles$) \times (100$ bases/molecule$)) = 6 \times 10^{16}$ bases. 10 Units of Exonuclease I should completely hydrolyze the aptamer candidate library if they lacked secondary structure. This enzyme is available from New England Biolabs at 20 or 200 Units per µl.

Exonuclease III may, in some embodiments, may be used to hydrolyze unbound oligos having blunt, or recessed 3' termini, including a stem loop, or handle (Xu and Evans, 2001; Parkinson and Lilley, 1997; White et al., 1997; Hadden et al., 2001). One unit is defined as the amount of enzyme required to produce 1 nmol of acid-soluble total nucleotide in a total reaction volume of 50 µl in 30 minutes at 37° C. One embodiment may begin with 1 nmol of oligonucleotide library. The weight of the starting material can be calculated as follows: $((30,000 \text{ g/mole}) \times (10^{-9} \text{ mole})) = 3 \times 10^{-5}$ g. 150 Units of Exonuclease III should completely hydrolyze the aptamer candidate library if they all had blunt, or 3' recessed, termini. This enzyme is available from New England Biolabs at 100 Units per µl.

As the above calculations show, in theory, a single cycle of Exonuclease I and Exonuclease III degradation will be required to hydrolyze the target below the threshold of PCR amplification. In practice it may require more than one cycle. If required, this cycling may be accomplished by either separating aptamer/target complexes, or by liberating aptamers from the target with increased temperature and passing the reaction, after the first digestion, through Qiagen's Nucleotide Removal Kit (Cat. No. 28304) with a buffer exchange. This column is designed for the removal of primers less than 10-mer, proteins, salts and unincorporated nucleotides. Oligos of 15-mer and larger are retained providing yet another means to exclude aptamer candidates that were unbound to their target and therefore digested. After clean up, incubation with the target may be reestablished under more stringent conditions (e.g. higher temperature) and the nuclease degradation step is repeated. In an embodiment, aptamers may be selected with three cycles, one at RT, one at 31° C. and one at 37° C.

Exonuclease III may hydrolyze the secondary structure of target-bound aptamers having a loose association with thrombin or other targets of interest. This means that some perfectly good aptamers will be lost. On the other hand, one might predict that these aptamers do not have the binding affinity and specificity of bound aptamers that are resistant to hydrolysis by Exonuclease III. As noted above, the law of mass action makes it difficult to select against weak binders with a single cycle of SELEX. The action of Exonuclease III on weakly associated binders may reduce this technical barrier, providing a major opportunity to select good aptamers with many fewer cycles than are required by SELEX. If aptamer recovery is not accomplished in 1 to 3 cycles, the procedure may be performed for up to about 30 rounds of selection, separation and amplification or more, if conditions warrant. The length of the handle will need to be optimized, since if the handle is too long, it might be hydrolyzed even if the apatmer/target complex has formed. The length of the primers used during amplification will also need to be optimized, since if the handle is not completely digested, the partially digested aptamer candidates that should be excluded from selection may still be amplified, albeit at a lower level. Accordingly, it will be necessary to optimize these two factors in a coordinated manner. It stands to reason that the Lariat Aptamer technique may have less utility with very small targets than with larger targets.

Example 4

In another example, DNAse I may be used to digest unbound aptamer candidates. DNase I is an endonuclease that nonspecifically cleaves DNA to release di-, tri- and oligo-nucleotide products with 5'-phosphorylated and 3'-hydroxylated ends. DNase I acts on single- and double-stranded DNA. It is commonly used in the laboratory technique known as DNAse I Footprinting, so it is good choice for selecting DNA that is bound to a target, for example a protein target. After incubation of the library to the target molecule and digestion with DNase I, DNase I may be heat inactivated.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Included herein is a Sequence Listing.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the claims appended hereto.

REFERENCES

Allen, P., Worland, S., Gold, L., 1995. Isolation of high-affinity rna ligands to Hiv-1 integrase from A random pool. Virology 209, 327-336.

Andre, C., Berthelot, A., Thomassin, M., Guillaume, Y. C., 2006. Enantiose-lective aptameric molecular recognition material: design of a novel chiral stationary phase for enantioseparation of a series of chiral herbicides by capillary electrochromatography. Electrophoresis 27, 3254-3262.

Andreola, M. L., Calmels, C., Michel, J., Toulme, J. J., Litvak, S., 2000. Towards the selection of phosphorothioate aptamers-optimizing in vitro selection steps with phosphorothioate nucleotides. Eur. J. Biochem. 267, 5032-5040.

Andreola, M. L., Pileur, F., Calmels, C., Ventura, M., Tarrago-Litvak, L., Toulme, J. J., Litvak, S., 2001. DNA aptamers selected against the HIV-1 RNase H display in vitro antiviral activity. Biochemistry 40, 10087-10094.

Asai, R., Nishimura, S. I., Aita, T., Takahashi, K., 2004. In vitro selection of DNA aptamers on chips using a method for generating point mutations. Anal. Lett. 37, 645-656.

Beinoraviciute-Kellner, R., Lipps, G., Krauss, G., 2005. In vitro selection of DNA binding sites for ABF1 protein from *Saccharomyces cerevisiae*. FEBS Lett. 579, 4535-4540.

Berens, C., Thain, A., Schroeder, R., 2001. A tetracycline-binding RNA aptamer. Bioorg. Med. Chem. 9, 2549-2556.

Berezovski, M., Musheev, M., Drabovich, A., Krylov, S. N., 2006. Non-SELEX selection of aptamers. J. Am. Chem. Soc. 128, 1410-1411.

Bianchini, M., Radrizzani, M., Brocardo, M. G., Reyes, G. B., Gonzalez, S. C., Santa-Coloma, T. A., 2001. Specific oligobodies against ERK-2 that recognize both the native and the denatured state of the protein. J. Immunol. Methods 252, 191-197.

Biesecker, G., Dihel, L., Enney, K., Bendele, R. A., 1999. Derivation of RNA aptamer inhibitors of human complement C5. Immunopharmacology 42, 219-230.

Bittker, J. A., Le, B. V., Liu, D. R., 2002. Nucleic acid evolution and minimization by nonhomologous random recombination. Nat. Biotechnol. 20, 1024-1029.

Blank, M., Weinschenk, T., Priemer, M., Schluesener, H., 2001. Systematic evolution of a DNA aptamer binding to rat brain tumor microvessels—selective targeting of endothelial regulatory protein pigpen. J. Biol. Chem. 276, 16464-16468.

Bock, L. C., Griffin, L. C., Latham, J. A., Vermaas, E. H., Toole, J. J., 1992. Selection of single-stranded DNA molecules that bind and inhibit human thrombin. Nature 355, 564-566.

Boiziau, C., Dausse, E., Yurchenko, L., Toulme, J. J., 1999. DNA aptamers selected against the HIV-1 trans-activation-responsive RNA element form RNA-DNA kissing complexes. J. Biol. Chem. 274, 12730-12737.

Bridonneau, P., Chang, Y. F., Buvoli, V. B., O'Connell, D., Parma, D., 1999. Site-directed selection of oligonucleotide antagonists by competitive elution. Antisens. Nucleic A 9, 1-11.

Brockstedt, U., Uzarowska, A., Montpetit, A., Pfau, W., Labuda, D., 2004. In vitro evolution of RNA aptamers recognizing carcinogenic aromatic amines. Biochem. Biophys. Res. Commun. 313, 1004-1008.

Brody, E. N., Willis, M. C., Smith, J. D., Jayasena, S., Zichi, D., Gold, L., 1999. The use of aptamers in large arrays for molecular diagnostics. Mol. Diagn. 4, 381-388.

Brown, D., Brown, J., Kang, C. H., Gold, L., Allen, P., 1997. Single-stranded RNA recognition by the bacteriophage T4 translational repressor, RegA. J. Biol. Chem. 272, 14969-14974.

Bruno, J. G., 1997. In vitro selection of DNA to chloroaromatics using magnetic microbead-based affinity separation and fluorescence detection. Biochem. Biophys. Res. Commun. 234, 117-120.

Bruno, J. G., Kiel, J. L., 1999. In vitro selection of DNA aptamers to anthrax spores with electrochemiluminescence detection. Biosens. Bioelectron. 14, 457-464.

Burgstaller, P., Famulok, M., 1994. Isolierung von RNA Aptameren für biolo-gische Cofaktoren durch in-vitro Selektion. Angew. Chem. 106, 1163-1166.

Burgstaller, P., Girod, A., Blind, M., 2002. Aptamers as tools for target prioritization and lead identification. Drug Discov. Today 7, 1221-1228.

Burke, D. H., Gold, L., 1997. RNA aptamers to the adenosine moiety of S— adenosyl methionine: structural inferences from variations on a theme and the reproducibility of SELEX. Nucleic Acids Res. 25, 2020-2024.

Burke, D. H., Hoffman, D. C., Brown, A., Hansen, M., Pardi, A., Gold, L., 1997. RNA aptamers to the peptidyl transferase inhibitor chloramphenicol. Chem. Biol. 4, 833-843.

Burke, D. H., Scates, L., Andrews, K., Gold, L., 1996. Bent pseudoknots and novel RNA inhibitors of type 1 human immunodeficiency virus (HIV-1) reverse transcriptase. J. Mol. Biol. 264, 650-666.

Burke, D. H., Willis, J. H., 1998. Recombination, RNA evolution, and bifunctional RNA molecules isolated through chimeric SELEX. RNA 4, 1165-1175.

Burmeister, P. E., Lewis, S. D., Silva, R. F., Preiss, J. R., Horwitz, L. R., Pender-grast, P. S., McCauley, T. G., Kurz, J. C., Epstein, D. M., Wilson, C., Keefe, A. D., 2005. Direct in vitro selection of a 20-O-methyl aptamer to VEGF. Chem. Biol. 12, 25-33.

Cassiday, L. A., Maher, L. J., 2003. Yeast genetic selections to optimize RNA decoys for transcription factor NF-kappa B. Proc. Natl. Acad. Sci. U.S.A. 100, 3930-3935.

Chaloin, L., Lehmann, M. J., Sczakiel, G., Restle, T., 2002. Endogenous expression of a high-affinity pseudoknot RNA aptamer suppresses replication of HIV-1. Nucleic Acids Res. 30, 4001-4008.

Chapman, J. A., Beckey, C., 2006. Pegaptanib: a novel approach to ocular neovascularization. Ann. Pharmacother. 40, 1322-1326.

Chen, L., Yun, S. W., Seto, J., Liu, W., Toth, M., 2003. The fragile X mental retardation protein binds and regulates a novel class of mRNAs containing U rich target sequences. Neuroscience 120, 1005-1017.

Chenna, R., Sugawara, H., Koike, T., Lopez, R., Gibson, T. J., Higgins, D. G., Thompson, J. D., 2003. Multiple sequence alignment with the clustal series of programs. Nucleic Acids Res. 31, 3497-3500.

Cho, J. S., Lee, Y. J., Shin, K. S., Jeong, S. J., Park, J., Lee, S. W., 2004a. In vitro selection of specific RNA aptamers for the NFAT DNA binding domain. Mol. Cells 18, 17-23.

Cho, S., Lee, S. H., Chung, W. J., Kim, Y. K., Lee, Y. S., Kim, B. G., 2004b. Microbead-based of chromatography chip using RNA aptamer modified with photocleavable linker. Electrophoresis 25, 3730-3739.

Chung, W. J., Kim, M. S., Cho, S., Park, S. S., Kim, J. H., Kim, Y. K., Kim, B. G., Lee, Y. S., 2005. Microaffinity purification of proteins based on photolytic elution: toward an efficient microbead affinity chromatography on a chip. Electrophoresis 26, 694-702.

Ciesiolka, J., Gorski, J., Yarus, M., 1995. Selection of an RNA domain that binds Zn2+. RNA 1, 538-550.

Clark, S. L., Remcho, V. T., 2002. Aptamers as analytical reagents. Electrophoresis 23, 1335-1340.

Connor, A. C., McGown, L. B., 2006. Aptamer stationary phase for protein capture in affinity capillary chromatography. J. Chromatogr. A 1111, 115-119.

Conrad, R. C., Baskerville, S., Ellington, A. D., 1995. In vitro selection methodologies to probe RNA function and structure. Mol. Div. 1, 69-78. Coulter, L. R., Landree, M. A., Cooper, T. A., 1997. Identification of a new class of exonic splicing enhancers by in vivo selection. Mol. Cell. Biol. 17, 2143-2150.

Cox, J. C., Ellington, A. D., 2001. Automated selection of anti-protein aptamers. Bioorg. Med. Chem. 9, 2525-2531.

Cox, J. C., Hayhurst, A., Hesselberth, J., Bayer, T. S., Georgiou, G., Ellington, A. D., 2002a. Automated selection of aptamers against protein targets translated in vitro: from gene to aptamer. Nucleic Acids Res. 30, e108.

Cox, J. C., Rudolph, P., Ellington, A. D., 1998. Automated RNA selection. Biotechnol. Prog. 14, 845-850.

Cox, J. C., Rajendran, M., Riedel, T., Davidson, E. A., Sooter, L. J., Bayer, T. S., Schmitz-Brown, M., Ellington, A. D., 2002b. Automated acquisition of aptamer sequences. Comb. Chem. High T. Scr. 5, 289-299.

Dang, C., Jayasena, S. D., 1996. Oligonucleotide inhibitors of Taq DNA polymerase facilitate detection of low copy number targets by PCR. J. Mol. Biol. 264, 268-278.

Daniels, D. A., Chen, H., Hicke, B. J., Swiderek, K. M., Gold, L., 2003. A tenascin-C aptamer identified by tumor cell SELEX: systematic evolution of ligands by exponential enrichment. Proc. Natl. Acad. Sci. U.S.A. 100, 15416-15421.

Daniels, D. A., Sohal, A. K., Rees, S., Grisshammer, R., 2002. Generation of RNA aptamers to the G-protein-coupled receptor for neurotensin, NTS-1. Anal. Biochem. 305, 214-226.

Darfeuille, F., Hansen, J. B., Orum, H., Primo, C. D., Toulme, J. J., 2004. LNA/DNA chimeric oligomers mimic RNA aptamers targeted to the TAR RNA element of HIV-1. Nucleic Acids Res. 32, 3101-3107.

Davis, J. H., Szostak, J. W., 2002. Isolation of high-affinity GTP aptamers from partially structured RNA libraries. Proc. Natl. Acad. Sci. U.S.A. 99, 11616-11621.

Davis, K. A., Abrams, B., Lin, Y., Jayasena, S. D., 1997. Use of a high affinity DNA ligand in flow cytometry (Reprinted from Nucleic Acids Research). J. Clin. Ligand Assay 20, 90-97.

Davis, K. A., Lin, Y., Abrams, B., Jayasena, S. D., 1998. Staining of cell surface human CD4 with 20-F-pyrimidine-containing RNA aptamers for flow cytometry. Nucleic Acids Res. 26, 3915-3924.

Deng, Q., German, I., Buchanan, D., Kennedy, R. T., 2001. Retention and separation of adenosine and analogues by affinity chromatography with an aptamer stationary phase. Anal. Chem. 73, 5415-5421.

Dobbelstein, M., Shenk, T., 1995. In-vitro selection of rna ligands for the ribosomal L22 protein associated with Epstein-Barr virus-expressed RNA by using randomized and cDNA-derived RNA libraries. J. Virol. 69, 8027-8034.

Dougan, H., Lyster, D. M., Vo, C. V., Stafford, A., Weitz, J. I., Hobbs, J. B., 2000. Extending the lifetime of anticoagulant oligodeoxynucleotide aptamers in blood. Nucl. Med. Biol. 27, 289-297.

Drabovich, A. P., Berezovski, M., Okhonin, V., Krylov, S. N., 2006. Selection of smart aptamers by methods of kinetic capillary electrophoresis. Anal. Chem. 78, 3171-3178.

Drolet, D. W., MoonMcDermott, L., Romig, T. S., 1996. An enzyme-linked oligonucleotide assay. Nat. Biotechnol. 14, 1021-1025.

Duconge, F., Toulme, J. J., 1999. In vitro selection identifies key determinants for loop-loop interactions: RNA aptamers selective for the TAR RNA element of HIV-1. RNA-A 5, 1605-1614.

Dyke, C. K., Steinhubl, S. R., Kleiman, N. S., Cannon, R. O., Aberle, L. G., Lin, M., Myles, S. K., Melloni, C., Harrington, R. A., 2006. First-in-human experience of an antidote-controlled anticoagulant using RNA aptamer technology. Circulation 114, 2490-2497.

Ellington, A. D., Szostak, J. W., 1990. In vitro selection of RNA molecules that bind specific ligands. Nature 346, 818-822.

Ellington, A. D., Szostak, J. W., 1992. Selection in vitro of single-stranded DNA molecules that fold into specific ligand-binding structures. Nature 355, 850-852.

Eulberg, D., Buchner, K., Maasch, C., Klussmann, S., 2005. Development of an automated in vitro selection protocol to obtain RNA-based aptamers: identification of a biostable substance P antagonist. Nucleic Acids Res. 33, e45.

Eulberg, D., Klussmann, S., 2003. Spiegelmers: biostable aptamers. Chembio-chemistry 4, 979-983.

Famulok, M., 1994. Molecular recognition of amino-acids by RNA-aptamers—an L-citrulline binding RNA motif and its evolution into an L-arginine binder. J. Am. Chem. Soc. 116, 1698-1706.

Famulok, M., 1999. Oligonucleotide aptamers that recognize small molecules. Curr. Opin. Struct. Biol. 9, 324-329.

Famulok, M., Blind, M., Mayer, G., 2001. Intramers as promising new tools in functional proteomics. Chem. Biol. 8, 931-939.

Famulok, M., Szostak, J. W., 1992. Stereospecific recognition of tryptophan agarose by in vitro selected RNA. J. Am. Chem. Soc. 114, 3990-3991.

Faulhammer, D., Eschgfaller, B., Stark, S., Burgstaller, P., Englberger, W., Erfurth, J., Kleinjung, F., Rupp, J., Vulcu, S. D., Schroder, W., Vonhoff, S., Nawrath, H., Gillen, C., Klussmann, S., 2004. Biostable aptamers with antagonistic properties to the neuropeptide nociceptin/orphanin FQ. RNA-A 10, 516-527.

Ferreira, C. S. M., Matthews, C. S., Missailidis, S., 2006. DNA aptamers that bind to MUC1 tumour marker: design and characterization of MUC1-binding single-stranded DNA aptamers. Tumor Biol. 27, 289-301.

Fitzwater, T., Polisky, B., 1996. A SELEX primer. Methods Enzymol. 267, 275-301.

Forster, C., Brauer, A. B. E., Brode, S., Schmidt, K. S., Perbandt, M., Meyer, A., Rypniewski, W., Betzel, C., Kurreck, J., Furste, J. P., Erdmann, V. A., 2006. Comparative crystallization and preliminary X-ray diffraction studies of locked nucleic acid and RNA stems of a tenascin C-binding aptamer. Acta Crystallogr. F 62, 665-668.

Fukusaki, E., Kato, T., Maeda, H., Kawazoe, N., Ito, Y., Okazawa, A., Kajiyama, S., Kobayashi, A., 2000. DNA aptamers that bind to chitin. Bioorg. Med. Chem. Lett. 10, 423-425.

Gebhardt, K., Shokraei, A., Babaie, E., Lindqvist, B. H., 2000. RNA aptamers to S-adenosylhomocysteine: kinetic properties, divalent cation dependency, and comparison with anti-5-adenosylhomocysteine antibody. Biochemistry 39, 7255-7265.

Geiger, A., Burgstaller, P., von der Eltz, H., Roeder, A., Famulok, M., 1996. RNA aptamers that bind L-arginine with sub-micromolar dissociation constants and high enantioselectivity. Nucleic Acids Res. 24, 1029-1036.

German, I., Buchanan, D. D., Kennedy, R. T., 1998. Aptamers as ligands in affinity probe capillary electrophoresis. Anal. Chem. 70, 4540-4545.

Gold, L., Brown, D., He, Y. Y., Shtatland, T., Singer, B. S., Wu, Y., 1997a. From oligonucleotide shapes to genomic SELEX: novel biological regulatory loops. Proc. Natl. Acad. Sci. U.S.A. 94, 59-64.

Gold, L., Polisky, B., Uhlenbeck, O., Yarus, M., 1995. Diversity of oligonucleotide functions. Annu. Rev. Biochem. 64, 763-797.

Gold, L., Singer, B., He, Y. Y., Brody, E., 1997b. SELEX and the evolution of genomes. Curr. Opin. Genet. Dev. 7, 848-851.

Golden, M. C., Collins, B. D., Willis, M. C., Koch, T. H., 2000. Diagnostic potential of PhotoSELEX-evolved ssDNA aptamers. J. Biotechnol. 81, 167-178.

Gopinath, S. C., 2007. Methods developed for SELEX. Anal. Bioanal. Chem. 387, 171-182.

Gopinath, S. C. B., Misono, T. S., Kawasaki, K., Mizuno, T., Imai, M., Odagiri, T., Kumar, P. K. R., 2006. An RNA aptamer that distinguishes between closely related human influenza viruses and inhibits haemagglutinin-mediated membrane fusion. J. Gen. Virol. 87, 479-487.

Goringer, H. U., Homann, M., Lorger, M., 2003. In vitro selection of high-affinity nucleic acid ligands to parasite target molecules. Int. J. Parasitol. 33, 1309-1317.

Grate, D., Wilson, C., 2001. Inducible regulation of the S-cerevisiae cell cycle mediated by an RNA aptamer-ligand complex. Bioorg. Med. Chem. 9, 2565-2570.

Green, L. S., Jellinek, D., Bell, C., Beebe, L. A., Feistner, B. D., Gill, S. C., Jucker, F. M., Janjic, N., 1995. Nuclease-resistant nucleic-acid ligands to vascular-permeability factor vascular endothelial growth-factor. Chem. Biol. 2, 683-695.

Green, L. S., Jellinek, D., Jenison, R., Ostman, A., Heldin, C. H., Janjic, N., 1996. Inhibitory DNA ligands to platelet-derived growth factor B-chain. Biochemistry 35, 14413-14424.

Guthold, M., Cubicciotti, R., Superfine, R., Taylor, R. M., 2002. Novel methodology to detect, isolate, amplify and characterize single aptamer molecules with desirable target-binding properties. Biophys. J. 82, 163A-1163A.

Guthrie, J. W., Hamula, C. L. A., Zhang, H. Q., Le, X. C., 2006. Assays for cytokines using aptamers. Methods 38, 324-330.

Haes, A. J., Giordano, B. C., Collins, G. E., 2006. Aptamer-based detection and quantitative analysis of ricin using affinity probe capillary electrophoresis. Anal. Chem. 78, 3758-3764.

Haller, A. A., Sarnow, P., 1997. In vitro selection of a 7-methyl-guanosine binding RNA that inhibits translation of capped mRNA molecules. Proc. Natl. Acad. Sci. U.S.A. 94, 8521-8526.

Harada, K., Frankel, A. D., 1995. Identification of two novel arginine binding DNAs. EMBO J. 14, 5798-5811.

Held, D. M., Greathouse, S. T., Agrawal, A., Burke, D. H., 2003. Evolutionary landscapes for the acquisition of new ligand recognition by RNA aptamers. J. Mol. Evol. 57, 299-308.

Hendry, P., Hannan, G., 1996. Detection and quantitation of unlabeled nucleic acids in polyacrylamide gels. Biotechniques 20, 258-264.

Hermann, T., Patel, D. J., 2000. Adaptive recognition by nucleic acid aptamers. Science 287, 820-825.

Herr, J. K., Smith, J. E., Medley, C. D., Shangguan, D. H., Tan, W. H., 2006. Aptamer-conjugated nanoparticles for selective collection and detection of cancer cells. Anal. Chem. 78, 2918-2924.

Hesselberth, J. R., Miller, D., Robertus, J., Ellington, A. D., 2000. In vitro selection of RNA molecules that inhibit the activity of ricin A-chain. J. Biol. Chem. 275, 4937-4942.

Hicke, B. J., Stephens, A. W., Gould, T., Chang, Y. F., Lynott, C. K., Heil, J., Borkowski, S., Hilger, C. S., Cook, G., Warren, S., Schmidt, P. G., 2006. Tumor targeting by an aptamer. J. Nucl. Med. 47, 668-678.

Hicke, B. J., Stephens, A. W., 2000. Escort aptamers: a delivery service for diadnosis and therapy. J. Clin. Invest. 106, 923-928.

Hicke, B. J., Marion, C., Chang, Y. F., Gould, T., Lynott, C. K., Parma, D., Schmidt, P. G., Warren, S., 2001. tenascin-c aptamers are generated using tumor cells and purified protein. J. Biol. Chem. 276, 48644-48654.

Hicke, B. J., Watson, S. R., Koenig, A., Lynott, C. K., Bargatze, R. F., Chang, Y. F., Ringquist, S., Moon-McDermott, L., Jennings, S., Fitzwater, T., Han, H. L., Varki, N., Albinana, I., Willis, M. C., Varki, A., Parma, D., 1996. DNA aptamers block L-selectin function in vivo. Inhibition of human lymphocyte trafficking in SCID mice. J. Clin. Invest. 98, 2688-2692.

Hirao, I., Harada, Y., Nojima, T., Osawa, Y., Masaki, H., Yokoyama, S., 2004. In vitro selection of RNA aptamers that bind to colicin E3 and structurally resemble the decoding site of 16S ribosomal RNA. Biochemistry 43, 3214-3221.

Hofmann, H. P., Limmer, S., Hornung, V., Sprinzl, M., 1997. Ni2+-binding RNA motifs with an asymmetric purine-rich internal loop and a G-A base pair. RNA 3, 1289-1300.

Homann, M., Go☐ringer, H. U., 1999. Combinatorial selection of high affinity RNA ligands to live African trypanosomes. Nucleic Acids Res. 27, 2006-2014.

Horn, W. T., Convery, M. A., Stonehouse, N. J., Adams, C. J., Liljas, L., Phillips, S. E. V., Stockley, P. G., 2004. The crystal structure of a high affinity RNA stem-loop complexed with the bacteriophage MS2 capsid: further challenges in the modeling of ligand-RNA interactions. RNA-A 10, 1776-1782.

Huang, Z., Szostak, J. W., 2003. Evolution of aptamers with secondary structures from a new specificity and new an ATP aptamer. RNA-A 9, 1456-1463.

Huizenga, D. E., Szostak, J. W., 1995. A DNA aptamer that binds adenosine and ATP. Biochemistry. 34, 656-665.

Hwang, B., Lee, S. W., 2002. Improvement of RNA aptamer activity against myasthenic autoantibodies by extended sequence selection. Biochem. Biophys. Res. Commun. 290, 656-662.

Hybarger, G., Bynum, J., Williams, R. F., Valdes, J. J., Chambers, J. P., 2006. A microfluidic SELEX prototype. Anal. Bioanal. Chem. 384, 191-198.

Ito, Y., Fukusaki, E., 2004. DNA as a 'nanomaterial'. J. Mol. Catal. B. 28, 155-166.

James, W., 2000. Aptamers. In: Meyers, R. A. (Ed.), Encyclopedia of Analytical Chemistry. John Wiley & Sons Ltd., Chichester, pp. 4848-4871.

Jayasena, S. D., 1999. Aptamers: an emerging class of molecules that rival antibodies in diagnostics. Clin. Chem. 45, 1628-1650.

Jellinek, D., Green, L. S., Bell, C., Janjic, N., 1994. Inhibition of receptor binding by high-affinity RNA ligands to vascular endothelial growth factor. Biochemistry 33, 10450-10456.

Jenison, R. D., Gill, S. C., Pardi, A., Polisky, B., 1994. High-resolution molecular discrimination by RNA. Science 263, 1425-1429.

Jensen, K. B., Atkinson, B. L., Willis, M. C., Koch, T. H., Gold, L., 1995. Using in vitro selection to direct the covalent attachment of human immunodeficiency virus type 1 Rev protein to high-affinity RNA ligands. Proc. Natl. Acad. Sci. U.S.A. 92, 12220-12224.

Jeon, S. H., Kayhan, B., Ben-Yedidia, T., Anion, R., 2004. A DNA aptamer prevents influenza infection by blocking the receptor binding region of the viral hemagglutinin. J. Biol. Chem. 279, 48410-48419.

Jeong, S., Eom, T., Kim, S., Lee, S., Yu, J., 2001. In vitro selection of the RNA aptamer against the Sialyl Lewis X and its inhibition of the cell adhesion. Biochem. Biophys. Res. Commun. 281, 237-243.

Jhaveri, S., Rajendran, M., Ellington, A. D., 2000. In vitro selection of signaling aptamers. Nat. Biotechnol. 18, 1293-1297.

Jhaveri, S., Olwin, B., Ellington, A. D., 1998. In vitro selection of phosphor-othiolated aptamers. Bioorg. Med. Chem. Lett. 8, 2285-2290.

Jiang, L., Sun, A. K., Fiala, R., Patel, D. J., 1997. Saccharide-RNA recognition in an aminoglycoside antibiotic-RNA aptamer complex. Chem. Biol. 4, 35-50.

Johnson, L., Gershon, P. D., 1999. RNA binding characteristics and overall topology of the vaccinia poly(A) polymerase-processivity factor-primer complex. Nucleic Acids Res. 27, 2708-2721.

Jones, L. A., Clancy, L. E., Rawlinson, W. D., White, P. A., 2006. High-affinity aptamers to subtype 3a hepatitis C virus polymerase display genotypic specificity. Antimicrob. Agents Ch. 50, 3019-3027.

Kato, T., Takemura, T., Yano, K., Ikebukuro, K., Karube, I., 2000. In vitro selection of DNA aptamers which bind to cholic acid. Biochim. Biophys. Acta 1493, 12-18.

Kawakami, J., Imanaka, H., Yokota, Y., Sugimoto, N., 2000. In vitro selection of aptamers that act with Zn2+. J. Inorg. Biochem. 82, 197-206.

Kawazoe, N., Ito, Y., Imanishi, Y., 1996. Patterned staining by fluorescein-labeled oligonucleotides obtained by in vitro selection. Anal. Chem. 68, 4309-4311.

Kelly, J. A., Feigon, J., Yeates, T. O., 1996. Reconciliation of the X-ray and NMR structures of the thrombin-binding aptamer d(GGTTGGTGTGGTTGG). J. Mol. Biol. 256, 417-422.

Kiga, D., Futamura, Y., Sakamoto, K., Yokoyama, S., 1998. An RNA aptamer to the xanthine/guanine base with a distinctive mode of purine recognition. Nucleic Acids Res. 26, 1755-1760.

Kikuchi, K., Umehara, T., Fukuda, K., Hwang, J., Kuno, A., Hasegawa, T., Ni shikawa, S., 2003. RNA aptamers targeted to domain II of hepatitis C virus IRES that bind to its apical loop region. J. Biochem. 133, 263-270.

Kim, S. J., Kim, M. Y., Lee, J. H., You, J. C., Jeong, S., 2002. Selection and stabilization of the RNA aptamers against the human immunodeficiency virus type-1 nucleocapsid protein. Biochem. Biophys. Res. Commun. 291, 925-931.

Kimoto, M., Endo, M., Mitsui, T., Okuni, T., Hirao, I., Yokoyama, S., 2004. Site-specific incorporation of a photo-crosslinking component into RNA by T7 transcription mediated by unnatural base pairs. Chem. Biol. 11, 47-55.

Kimoto, M., Shirouzu, M., Mizutani, S., Koide, H., Kaziro, Y., Hirao, I., Yokoyama, S., 2002. Anti-(Raf-1) RNA aptamers that inhibit Ras-induced Raf-1 activation. Eur. J. Biochem. 269, 697-704.

King, D. J., Bassett, S. E., Li, X., Fennewald, S. A., Herzog, N. K., Luxon, B. A., Shope, R., Gorenstein, D. G., 2002. Combinatorial selection and binding of phosphorothioate aptamers targeting human NF-kappa B RelA(p65) and p50. Biochemistry 41, 9696-9706.

Kirby, R., Cho, E. J., Gehrke, B., Bayer, T., Park, Y. S., Neikirk, D. P., McDevitt, J. T., Ellington, A. D., 2004. Aptamer-based sensor arrays for the detection and quantitation of proteins. Anal. Chem. 76, 4066-4075.

Kleinjung, F., Klussmann, S., Erdmann, V. A., Scheller, F. W., Furste, J. P., Bier, F. F., 1998. High-affinity RNA as a recognition element in a biosensor. Anal. Chem. 70, 328-331.

Klug, S. J., Huttenhofer, A., Famulok, M., 1999. In vitro selection of RNA aptamers that bind special elongation factor SelB, a protein with multiple RNA-binding sites, reveals one major interaction domain at the carboxyl terminus. RNA 5, 1180-1190.

Klussmann, S., 2006. The Aptamer Handbook. Functional Oligonucleotides and Their Applications. WILEY-VCH Verlag GmbH & Co., KGaA, Wein-heim.

Klussmann, S., Nolte, A., Bald, R., Erdmann, V. A., Furste, J. P., 1996. Mirror-image RNA that binds D-adenosine. Nat. Biotechnol. 14, 1112-1115.

Ko, J., Lee, Y., Park, I., Cho, B., 2001. Identification of a structural motif of 23S rRNA interacting with 5S rRNA. FEBS Lett. 508, 300-304.

Ko, J. H., Cho, B., Alm, J. K., Lee, Y., Park, I., 1999. Probing the functional motifs of *Escherichia coli* 5S rRNA in relation to 16S rRNA using a SELEX experiment. Br. Kor. Chem. Soc. 20, 1335-1339.

Koizumi, M., Breaker, R. R., 2000. Molecular recognition of cAMP by an RNA aptamer. Biochemistry 39, 8983-8992.

Kopylov, A. M., Spiridonova, V. A., 2000. Combinatorial chemistry of nucleic acids: SELEX. Mol. Biol. 34, 940-954.

Kotia, R. B., Li, L., McGown, 2000. Separation of nontarget compounds by DNA aptamers. Anal. Chem. 72, 827-831.

Kubik, M. F., Bell, C., Fitzwater, T., Watson, S. R., Tasset, D. M., 1997. Isolation and characterization of 20-fluoro-, 20-amino-, and 20-fluoro/amino-modified RNA ligands to human IFN-gamma that inhibit receptor binding. J. Immunol. 159, 259-267.

Kumar, P. K. R., Machida, K., Urvil, P. T., Kakiuchi, N., Vishnuvardhan, D., Shimotohno, K., Taira, K., Nishikawa, S., 1997. Isolation of RNA aptamers specific to the NS3 protein of hepatitis C virus from a pool of completely random RNA. Virology 237, 270-282.

Kusser, W., 2000. Chemically modified nucleic acid aptamers for in vitro selections: evolving evolution. J. Biotechnol. 74, 27-38.

Kuwahara, M., Hanawa, K., Ohsawa, K., Kitagata, R., Ozaki, H., Sawai, H., 2006. Direct PCR amplification of various modified DNAs having amino acids: convenient preparation of DNA libraries with high-potential activities for in vitro selection. Bioorg. Med. Chem. 14, 2518-2526.

Kwon, M., Chun, S. M., Jeong, S., Yu, J., 2001. In vitro selection of RNA against kanamycin B. Mol. Cells. 11, 303-311.

Lato, S. M., Boles, A. R., Ellington, A. D., 1995. In-vitro selection of RNA lectins—using combinatorial chemistry to interpret ribozyme evolution. Chem. Biol. 2, 291-303.

Lato, S. M., Ellington, A. D., 1996. Screening chemical libraries for nucleic—acid-binding drugs by in vitro selection: a test case with lividomycin. Mol. Div. 2, 103-110.

Lauhon, C. T., Szostak, J. W., 1995. RNA aptamers that bind flavin and nicotinamide redox cofactors. J. Am. Chem. Soc. 117, 1246-1257.

Lee, J. F., Stovall, G. M., Ellington, A. D., 2006. Aptamer therapeutics advance. Curr. Opin. Chem. Biol. 10, 282-289.

Lee, M., Walt, D. R., 2000. A fiber-optic microarray biosensor using aptamers as receptors. Anal. Biochem. 282, 142-146.

Lee, S. K., Park, M. W., Yang, E. G., Yu, J. H., Jeong, S. J., 2005. An RNA aptamer that binds to the beta-catenin interaction domain of TCF-1 protein. Bio-chem. Biophys. Res. Commun. 327, 294-299.

Lee, Y. J., Lee, S. W., 2006. In vitro selection of cancer-specific RNA aptamers. J. Microbiol. Biotechnol. 16, 1149-1153.

Leva, S., Lichte, A., Burmeister, J., Man, P., Jahnke, B., Fesser, D., Erfurth, J., Burgstaller, P., Klussmann, S., 2002. GnRH binding RNA and DNA Spiegelmers: a novel approach toward GnRH antagonism. Chem. Biol. 9, 351-359.

Liss, M., Petersen, B., Wolf, H., Prohaska, E., 2002. An aptamer-based quartz crystal protein biosensor. Anal. Chem. 74, 4488-4495.

Liu, J. J., Stormo, G. D., 2005. Combining SELEX with quantitative assays to rapidly obtain accurate models of protein-DNA interactions. Nucleic Acids Res. 33, e141.

Liu, J. W., Lu, Y., 2006. Smart nanomaterials responsive to multiple chemical stimuli with controllable cooperativity. Adv. Mater. 18, 1667-1671.

Liu, X. M., Zhang, D. J., Cao, G. J., Yang, G., Ding, H. M., Liu, G., Fan, M., Shen, B. F., Shao, N. S., 2003. RNA aptamers specific for bovine thrombin. J. Mol. Recognit. 16, 23-27.

Lorsch, J. R., Szostak, J. W., 1994. In vitro selection of RNA aptamers specific for cyanocobalamin. Biochemistry 33, 973-982.

Lozupone, C., Changayil, S., Majerfeld, I., Yarus, M., 2003. Selection of the simplest RNA that binds isoleucine. RNA 9, 1315-1322.

Lupold, S. E., Hicke, B. J., Lin, Y., Coffey, D. S., 2002. Identification and characterization of nuclease-stabilized RNA molecules that bind human prostate cancer cells via the prostate-specific membrane antigen. Cancer Res. 62, 4029-4033.

Maberley, D., 2005. Pegaptanib for neovascular age-related macular degeneration. Issues Emerg. Health Technol. 1-4.

Macaya, R. F., Schultze, P., Smith, F. W., Roe, J. A., Feigon, J., 1993. Thrombin-binding DNA aptamer forms a unimolecular quadruplex structure in solution. Proc. Natl. Acad. Sci. U.S.A. 90, 3745-3749.

Majerfeld, I., Puthenvedu, D., Yarus, M., 2005. RNA affinity for molecular L-histidine; genetic code origins. J. Mol. Evol. 61, 226-235.

Majerfeld, I., Yarus, M., 1998. Isoleucine: RNA sites with associated coding sequences. RNA 4, 471-478.

Majerfeld, I., Yarus, M., 1994. An RNA pocket for an aliphatic hydrophobe. Nat. Struct. Mol. Biol. 1, 287-292.

Mallikaratchy, P., Stahelin, R. V., Cao, Z. H., Cho, W. H., Tan, W. H., 2006. Selection of DNA ligands for protein kinase C-delta. Chem. Commun. 3229-3231.

Mann, D., Reinemann, C., Stoltenburg, R., Strehlitz, B., 2005. In vitro selection of DNA aptamers binding ethanolamine. Biochem. Biophys. Res. Commun. 338, 1928-1934.

Mannironi, C., DiNardo, A., Fruscoloni, P., TocchiniValentini, G. P., 1997. In vitro selection of dopamine RNA ligands. Biochemistry 36, 9726-9734.

Marro, M. L., Daniels, D. A., McNamee, A., Andrew, D. P., Chapman, T. D., Jiang, M. S., Wu, Z. N., Smith, J. L., Patel, K. K., Gearing, K. L., 2005. Identification of potent and selective RNA antagonists of the IFN-gamma-inducible CXCL10 chemokine. Biochemistry 44, 8449-8460.

Marshall, K. A., Ellington, A. D., 2000. In vitro selection of RNA aptamers. Methods Enzymol. 318, 193-214.

Martell, R. E., Nevins, J. R., Sullenger, B. A., 2002. Optimizing aptamer activity for gene therapy applications using expression cassette SELEX. Mol. Ther. 6, 30-34.

Masud, M. M., Kuwahara, M., Ozaki, H., Sawai, H., 2004. Sialyllactose-binding modified DNA aptamer bearing additional functionality by SELEX. Bioorg. Med. Chem. 12, 1111-1120.

Meli, M., Vergne, J., Decout, J. L., Maurel, M. C., 2002. Adenine-aptamer complexes—A bipartite RNA site that binds the adenine nucleic base. J. Biol. Chem. 277, 2104-2111.

Mendonsa, S. D., Bowser, M. T., 2004. In vitro selection of high-affinity DNA ligands for human IgE using capillary electrophoresis. Anal. Chem. 76, 5387-5392.

Michaud, M., Jourdan, E., Villet, A., Ravel, A., Grosset, C., Peyrin, E., 2003. A DNA aptamer as a new target-specific chiral selector for HPLC. J. Am. Chem. Soc. 125, 8672-8679.

Misono, T. S., Kumar, P. K. R., 2005. Selection of RNA aptamers against human influenza virus hemagglutinin using surface plasmon resonance. Anal. Biochem. 342, 312-317.

Missailidis, S., Thomaidou, D., Borbas, K. E., Price, M. R., 2005. Selection of aptamers with high affinity and high specificity against C595, an anti-MUC1 IgG3 monoclonal antibody, for antibody targeting. J. Immunol. Methods 296, 45-62.

Morris, K. N., Jensen, K. B., Julin, C. M., Weil, M., Gold, L., 1998. High affinity ligands from in vitro selection: complex targets. Proc. Natl. Acad. Sci. U.S.A. 95, 2902-2907.

Mosing, R. K., Mendonsa, S. D., Bowser, M. T., 2005. Capillary electrophoresis—SELEX selection of aptamers with affinity for HIV-1 reverse transcriptase. Anal. Chem. 77, 6107-6112.

Mukhopadhyay, R., 2005. Aptamers are ready for the spotlight. Anal. Chem. 77, 114A-118A.

Murphy, M. B., Fuller, S. T., Richardson, P. M., Doyle, S. A., 2003. An improved method for the in vitro evolution of aptamers and applications in protein detection and purification. Nucleic Acids Res. 31, e110.

Naimuddin, M., Kitamura, K., Kinoshita, Y., Honda-Takahashi, Y., Murakami, M., Ito, M., Yamamoto, K., Hanada, K., Husimi, Y., Nishigaki, K., 2007. Selection-by-function: efficient enrichment of cathepsin E inhibitors from a DNA library. J. Mol. Recognit. 20, 58-68.

Nakamura, C., Kobayashi, T., Miyake, M., Shirai, M., Miyake, J., 2001. Usage of a DNA aptamer as a ligand targeting microcystin. Mol. Cryst. Liquid Cryst. 371, 369-374.

Nimjee, S. M., Rusconi, C. P., Harrington, R. A., Sullenger, B. A., 2005a. The potential of aptamers as anticoagulants. Trends Cardiovasc. Med. 15, 41-45. Nimjee, S. M., Rusconi, C. P., Sullenger, B. A., 2005b. Aptamers: an emerging class of therapeutics. Arum. Rev. Med. 56, 555-583.

Nishikawa, F., Funaji, K., Fukuda, K., Nishikawa, S., 2004. In vitro selection of RNA aptamers against the HCVNS3 helicase domain. Oligonucleotides 14, 114-129.

Nix, J., Sussman, D., Wilson, C., 2000. The 1.3 angstrom crystal structure of a biotin-binding pseudoknot and the basis for RNA molecular recognition. J. Mol. Biol. 296, 1235-1244.

Nutiu, R., Li, Y. F., 2005. In vitro selection of structure-switching signaling aptamers. Angew. Chem.-Int. Edit. 44, 1061-1065.

O'Sullivan, C. K., 2002. Aptasensors—the future of biosensing. Anal. Bioanal. Chem. 372, 44-48.

Ohuchi, S. P., Ohtsu, T., Nakamura, Y., 2006. Selection of RNA aptamers against recombinant transforming growth factor-beta type III receptor displayed on cell surface. Biochimie 88, 897-904.

Okazawa, A., Maeda, H., Fukusaki, E., Katakura, Y., Kobayashi, A., 2000. In vitro selection of hematoporphyrin binding DNA aptamers. Bioorg. Med. Chem. Lett. 10, 2653-2656.

Pan, W., Craven, R. C., Qiu, Q., Wilson, C. B., Wills, J. W., Golovine, S., Wang, J. F., 1995. Isolation of virus-neutralizing RNAs from a large pool of random sequences. Proc. Natl. Acad. Sci. U.S.A. 92, 11509-11513.

Patel, D. J., 1997. Structural analysis of nucleic acid aptamers. Curr. Opin. Chem. Biol. 1, 32-46.

Patel, D. J., Suri, A. K., Jiang, F., Jiang, L. C., Fan, P., Kumar, R. A., Nonin, S., 1997. Structure, recognition and adaptive binding in RNA aptamer complexes. J. Mol. Biol. 272, 645-664.

Petersen, M., Wengel, J., 2003. LNA: a versatile tool for therapeutics and genomics. Trends Biotechnol. 21, 74-81.

Pileur, F., Andreola, M. L., Dausse, E., Michel, J., Moreau, S., Yamada, H., Gaidamakov, S. A., Crouch, R. J., Toulme, J. J., Cazenave, C., 2003. Selective inhibitory DNA aptamers of the human RNase H1. Nucleic Acids Res. 31, 5776-5788.

Potyrailo, R. A., Conrad, R. C., Ellington, A. D., Hieftje, G. M., 1998. Adapting selected nucleic acid ligands (aptamers) to biosensors. Anal. Chem. 70, 3419-3425.

Proske, D., Gilch, S., Wopfner, F., Schatzl, H. M., Winnacker, E. L., Famulok, M., 2002. Prion-protein-specific aptamer reduces PrPSc formation. Chem-biochemistry 3, 717-725.

Radrizzani, M., Broccardo, M., Solveyra, C. G., Bianchini, M., Reyes, G. B., Cafferata, E. G., Santa-Coloma, T. A., 1999. Oligobodies: bench made synthetic antibodies. Med.-Buenos Aires 59, 753-758.

Rajendran, M., Ellington, A. D., 2003. In vitro selection of molecular beacons. Nucleic Acids Res. 31, 5700-5713.

Ravelet, C., Grosset, C., Peyrin, E., 2006. Liquid chromatography, electro-chromatography and capillary electrophoresis applications of DNA and RNA aptamers. J. Chromatogr. A 1117, 1-10.

Rhie, A., Kirby, L., Sayer, N., Wellesley, R., Disterer, P., Sylvester, I., Gill, A., Hope, J., James, W., Tahiri-Alaoui, A., 2003. Characterization of 20-fluoro-RNA aptamers that bind preferentially to disease-associated conformations of prion protein and inhibit conversion. J. Biol. Chem. 278, 39697-39705.

Rhodes, A., Deakin, A., Spaull, J., Coomber, B., Aitken, A., Life, P., Rees, S., 2000. The generation and characterization of antagonist RNA aptamers to human oncostatin M. J. Biol. Chem. 275, 28555-28561.

Rhodes, A., Smithers, N., Chapman, T., Parsons, S., Rees, S., 2001. The generation and characterisation of antagonist RNA aptamers to MCP-1. FEBS Lett. 506, 85-90.

Rimmele, M., 2003. Nucleic acid aptamers as tools and drugs: recent developments. Chembiochemistry 4, 963-971.

Ringquist, S., Jones, T., Snyder, E. E., Gibson, T., Boni, I., Gold, L., 1995. High-affinity RNA ligands to *Escherichia coli* ribosomes and ribosomal protein S1: comparison of natural and unnatural binding sites. Biochemistry 34, 3640-3648.

Roulet, E., Busso, S., Camargo, A. A., Simpson, A. J. G., Mermod, N., Bucher, P., 2002. High-throughput SELEX-SAGE method for quantitative modeling of transcription-factor binding sites. Nat. Biotechnol. 20, 831-835.

Rudman, J., Green, L. S., Beeson, J., Waugh, S., Gillette, W. L., Henninger, D. D., Claesson-Welsh, L., Janjic, N., 1998. 20-fluoropyrimidine RNA-based aptamers to the 165-amino acid form of vascular endothelial growth factor (VEGF(165))—inhibition of receptor binding and VEGF-induced vascular permeability through interactions requiring the exon 7-encoded domain. J. Biol. Chem. 273, 20556-20567.

Rusconi, C. P., Roberts, J. D., Pitoc, G. A., Nimjee, S. M., White, R. R., Quick, G., Scardino, E., Fay, W. P., Sullenger, B. A., 2004. Antidote-mediated control of an anticoagulant aptamer in vivo. Nat. Biotechnol. 22, 1423-1428.

Saito, T., Tomida, M., 2005. Generation of inhibitory DNA aptamers against human hepatocyte growth factor. DNA Cell Biol. 24, 624-633. Sampson, T., 2003. Aptamers and SELEX: the technology. World Patent Inf. 25, 123-129.

Saran, D., Frank, J., Burke, D. H., 2003. The tyranny of adenosine recognition among RNA aptamers to coenzyme A. BMC Evol. Biol. 3. Sassanfar, M., Szostak, J. W., 1993. An RNA motif that binds ATP. Nature 364, 550-553.

Sazani, P. L., Larralde, R, Szostak, J. W., 2004. A small aptamer with strong and specific recognition of the triphosphate of ATP. J. Am. Chem. Soc. 126, 8370-8371.

Scarabino, D., Crisari, A., Lorenzini, S., Williams, K., Tocchini-Valentini, G. P., 1999. tRNA prefers to kiss. EMBO J. 18, 4571-4578.

Schmidt, K. S., Borkowski, S., Kurreck, J., Stephens, A. W., Bald, R., Hecht, M., Friebe, M., Dinkelborg, L., Erdmann, V. A., 2004. Application of locked nucleic acids to improve aptamer in vivo stability and targeting function. Nucleic Acids Res. 32, 5757-5765.

Schneider, C., Suhnel, J., 1999. A molecular dynamics simulation of the flavin mononucleotide-RNA aptamer complex. Biopolymers 50, 287-302.

Schneider, D., Gold, L., Platt, T., 1993. Selective enrichment of RNA species for tight-binding to *Escherichia-Coli* Rho-factor. FASEB J. 7, 201-207.

Schneider, D. J., Feigon, J., Hostomsky, Z., Gold, L., 1995. High-affinity ssdna inhibitors of the reverse-transcriptase of type-1 human-immunodeficiency-virus. Biochemistry 34, 9599-9610.

Schurer, H., Stembera, K., Knoll, D., Mayer, G., Blind, M., Forster, H., Famulok, M., Wetzel, P., Hahn, U., 2001. Aptamers that bind to the antibiotic moenomycin A. Bioorg. Med. Chem. 9, 2557-2563.

Seiwert, S. D., Nahreini, T. S., Aigner, S., Alm, N. G., Uhlenbeck, O. C., 2000. RNA aptamers as pathway-specific MAP kinase inhibitors. Chem. Biol. 7, 833-843.

Sekiya, S., Noda, K., Nishikawa, F., Yokoyama, T., Kumar, P. K. R., Nishikawa, S., 2006. Characterization and application of a novel RNA aptamer against the mouse prion protein. J. Biochem. 139, 383-390.

Sekkal, D., Dausse, E., Di Primo, C., Darfeuille, F., Boiziau, C., Toulme, J. J., 2002. In vitro selection of DNA aptamers against the HIV-1 TAR RNA hairpin. Antisense Nucleic Acid Drug Dev. 12, 265-274.

Shangguan, D., Li, Y., Tang, Z. W., Cao, Z. H. C., Chen, H. W., Mallikaratchy, P., Sefah, K., Yang, C. Y. J., Tan, W. H., 2006. Aptamers evolved from live cells as effective molecular probes for cancer study. Proc. Natl. Acad. Sci. U.S.A. 103, 11838-11843.

Shi, H., Fan, X. C., Ni, Z. Y., L is, J. T., 2002. Evolutionary dynamics and population control during in vitro selection and amplification with multiple targets. RNA-A 8, 1461-1470.

Shimada, T., Fujita, N., Maeda, M., Ishihama, A., 2005. Systematic search for the Cra-binding promoters using genomic SELEX system. Genes Cells 10, 907-918.

Singer, B. S., Shtatland, T., Brown, D., Gold, L., 1997. Libraries for genomic SELEX. Nucleic Acids Res. 25, 781-786.

Smith, D., Kirschenheuter, G. P., Charlton, J., Guidot, D. M., Repine, J. E., 1995. In-vitro selection of RNA-based irreversible inhibitors of human neutrophil elastase. Chem. Biol. 2, 741-750.

Soukup, G. A., Breaker, R. R., 1999. Relationship between internucleotide linkage geometry and the stability of RNA. RNA-A 5, 1308-1325.

Srisawat, C., Engelke, D. R., 2001. Streptavidin aptamers: affinity tags for the study of RNAs and ribonucleoproteins. RNA 7, 632-641.

Srisawat, C., Goldstein, I. J., Engelke, D. R., 2001. Sephadex-binding RNA ligands: rapid affinity purification of RNA from complex RNA mixtures. Nucleic Acids Res. 29, E4.

Stelzl, U., Nierhaus, K. H., 2001. SERF: in vitro selection of random RNA fragments to identify protein binding sites within large RNAs. Methods 25, 351-357.

Stoltenburg, R., Reinemann, C., Strehlitz, B., 2007. SELEX—A "R"evolutionary method to generate high-affinity nucleic acid ligands Biomolecular Engineering 24 (2007) 381-403 403

Stojanovic, M. N., de Prada, P., Landry, D. W., 2000. Fluorescent sensors based on aptamer self-assembly. J. Am. Chem. Soc. 122, 11547-11548.

Stoltenburg, R., Reinemann, C., Strehlitz, B., 2005. FluMag-SELEX as an advantageous method for DNA aptamer selection. Anal. Bioanal. Chem. 383, 83-91.

Tahiri-Alaoui, A., Frigotto, L., Manville, N., Ibrahim, J., Romby, P., James, W., 2002. High affinity nucleic acid aptamers for streptavidin incorporated into bi-specific capture ligands. Nucleic Acids Res. 30, e45.

Takemura, K., Wang, P., Vorberg, I., Surewicz, W., Priola, S. A., Kanthasamy, A., Pottathil, R., Chen, S. G., Sreevatsan, S., 2006. DNA aptamers that bind to PrPC and not PrPSc show sequence and structure specificity. Exp. Biol. Med. 231, 204-214.

Tang, J. J., Xie, J. W., Shao, N. S., Yan, Y., 2006. The DNA aptamers that specifically recognize ricin toxin are selected by two in vitro selection methods. Electrophoresis 27, 1303-1311.

Tang, J., Yu, T., Guo, L., Xie, J., Shao, N., He, Z., 2007. In vitro selection of DNA aptamer against abrin toxin and aptamer-based abrin direct detection. Biosens. Bioelectron. 22, 2456-2463.

Theis, M. G., Knorre, A., Kellersch, B., Moelleken, J., Wieland, F., Kolanus, W., Famulok, M., 2004. Discriminatory aptamer reveals serum response element transcription regulated by cytohesin-2. Proc. Natl. Acad. Sci. U.S.A. 101, 11221-11226.

Thiel, K., 2004. Oligo oligarchy—the surprisingly small world of aptamers. Nat. Biotechnol. 22, 649-651.

Thompson, J. D., Higgins, D. G., Gibson, T. J., 1994. CLUSTAL W: improving the sensitivity of progressive multiple sequence alignment through sequence weighting, position-specific gap penalties and weight matrix choice. Nucleic Acids Res. 22, 4673-4680.

Tombelli, S., Minunni, A., Luzi, E., Mascini, M., 2005a. Aptamer-based biosensors for the detection of HIV-1 Tat protein. Bioelectrochemistry 67, 135-141.

Tombelli, S., Minunni, A., Mascini, A., 2005b. Analytical applications of aptamers. Biosens. Bioelectron. 20, 2424-2434.

Toulme, J. J., Darfeuille, F., Kolb, G. L., Chabas, S., Staedel, C., 2003. Modulating viral gene expression by aptamers to RNA structures. Biol. Cell. 95, 229-238.

Tsai, R. Y. L., Reed, R. R., 1998. Identification of DNA recognition sequences and protein interaction domains of the multiple-Zn-finger protein Roaz. Mol. Cell. Biol. 18, 6447-6456.

Tucker, C. E., Chen, L. S., Judkins, M. B., Farmer, J. A., Gill, S. C., Drolet, D. W., 1999. Detection and plasma pharmacokinetics of an anti-vascular endothelial growth factor oligonucleotide-aptamer (NX1838) in rhesus monkeys. J. Chromatogr. B 732, 203-212.

Tuerk, C., Gold, L., 1990. Systematic evolution of ligands by exponential enrichment: RNA ligands to bacteriophage T4 DNA polymerase. Science 249, 505-510.

Tuerk, C., Macdougal, S., Gold, L., 1992. RNA pseudoknots that inhibit human-immunodeficiency-virus type-1 reverse-transcriptase. Proc. Natl. Acad. Sci. U.S.A. 89, 6988-6992.

Ulrich, H., Magdesian, M. H., Alves, M. J. M., Colli, W., 2002. In vitro selection of RNA aptamers that bind to cell adhesion receptors of *Trypanosoma cruzi* and inhibit cell invasion. J. Biol. Chem. 277, 20756-20762.

Ulrich, H., Martins, A. H. B., Pesquero, J. B., 2004. RNA and DNA aptamers in cytomics analysis. Cytom. Part A. 59A, 220-231.

Ulrich, H., Trujillo, C. A., Nery, A. A., Alves, J. M., Majumder, P., Resende, R. R., Martins, A. H., 2006. DNA and RNA aptamers: from tools for basic research towards therapeutic applications. Comb. Chem. High Throughput Screen. 9, 619-632.

Vaish, N. K., Larralde, R., Fraley, A. W., Szostak, J. W., McLaughlin, L. W., 2003. A novel, modification-dependent ATP-binding aptamer selected from an RNA library incorporating a cationic functionality. Biochemistry 42, 8842-8851.

Vater, A., Jarosch, F., Buchner, K., Klussmann, S., 2003. Short bioactive Spiegelmers to migraine-associated calcitonin gene-related peptide rapidly identified by a novel approach: tailored-SELEX. Nucleic Acids Res. 31, e130.

Vianini, E., Palumbo, M., Gatto, B., 2001. In vitro selection of DNA aptamers that bind L-tyrosinamide. Bioorg. Med. Chem. 9, 2543-2548.

Walder, R. Y., Hayes, J. R., Walder, J. A., 1993. Use of PCR primers containing a 3'-terminal ribose residue to prevent cross-contamination of amplified sequences. Nucleic Acids Res. 21, 4339-4343.

Wallace, S. T., Schroeder, R., 1998. In vitro selection and characterization of streptomycin-binding RNAs: recognition discrimination between antibiotics. RNA 4, 112-123.

Wallis, M. G., von Ahsen, U., Schroeder, R., Famulok, M., 1995. A novel RNA motif for neomycin recognition. Chem. Biol. 2, 543-552.

Wang, C., Zhang, M., Yang, G., Zhang, D., Ding, H., Wang, H., Fan, M., Shen, B., Shao, N., 2003. Single-stranded DNA aptamers that bind differentiated but not parental cells: subtractive systematic evolution of ligands by exponential enrichment. J. Biotechnol. 102, 15-22.

Wang, Y., Rando, R. R., 1995. Specific binding of aminoglycoside antibiotics to RNA. Chem. Biol. 2, 281-290.

Wang X-L, Li F, Su Y-H, Sun X, Li X-B, Schluesener H J, Tang F and Xu S-Q, 2004. "Ultrasensitive Detection of Protein Using an Aptamer-Based Exonuclease Protection Assay", Anal Chem., 76(19), 5606.

Weiss, S., Proske, D., Neumann, M., Groschup, M. H., Kretzschmar, H. A., Famulok, M., Winnacker, E. L., 1997. RNA aptamers specifically interact with the prion protein PrP. J. Virol. 71, 8790-8797.

Wen, J. D., Gray, D. M., 2004. Selection of genomic sequences that bind tightly to Ff gene 5 protein: primer-free genomic SELEX. Nucleic Acids Res. 32, e182.

White, R., Rusconi, C., Scardino, E., Wolberg, A., Lawson, J., Hoffman, M., Sullenger, B., 2001. Generation of species cross-reactive aptamers using "toggle" SELEX. Mol. Ther. 4, 567-574.

White, R. R., Shan, S., Rusconi, C. P., Shetty, G., Dewhirst, M. W., Kontos, C. D., Sullenger, B. A., 2003. Inhibition of rat corneal angiogenesis by a nuclease-resistant RNA aptamer specific for angiopoietin-2. Proc. Natl. Acad. Sci. U.S.A. 100, 5028-5033.

Wiegand, T. W., Williams, P. B., Dreskin, S. C., Jouvin, M. H., Kinet, J. P., Tasset, D., 1996. High-affinity oligonucleotide ligands to human IgE inhibit binding to Fc epsilon receptor I. J. Immunol. 157, 221-230.

Williams, K. P., Bartel, D. P., 1995. PCR product with strands of unequal length. Nucleic Acids Res. 23, 4220-4221.

Williams, K. P., Liu, X. H., Schumacher, T. N., Lin, H. Y., Ausiello, D. A., Kim, P. S., Bartel, D. P., 1997. Bioactive and nuclease-resistant L-DNA ligand of vasopressin. Proc. Natl. Acad. Sci. U.S.A. 94, 11285-11290.

Wilson, C., Nix, J., Szostak, J., 1998. Functional requirements for specific ligand recognition by a biotin-binding RNA pseudoknot. Biochemistry 37, 14410-14419.

Wilson, C., Szostak, J., 1995. In vitro evolution of a self-alkylating ribozyme. Nature 374, 777-782.

Wilson, C., Szostak, J. W., 1998. Isolation of a fluorophore-specific DNA aptamer with weak redox activity. Chem. Biol. 5, 609-617.

Wilson, D. S., Szostak, J. W., 1999. In vitro selection of functional nucleic acids. Ann. Rev. Biochem. 68, 611-647.

Wu, L. H., Curran, J. F., 1999. An allosteric synthetic DNA. Nucleic Acids Res. 27, 1512-1516.

Yan, A. C., Bell, K. M., Breeden, M. M., Ellington, A. D., 2005. Aptamers: prospects in therapeutics and biomedicine. Front. Biosci. 10, 1802-1827.

Yang, Q., Goldstein, I. J., Mei, H. Y., Engelke, D. R., 1998. DNA ligands that bind tightly and selectively to cellobiose. Proc. Natl. Acad. Sci. U.S.A. 95, 5462-5467.

Yang, X. B., Li, X., Prow, T. W., Reece, L. M., Bassett, S. E., Luxon, B. A., Herzog, N. K., Aronson, J., Shope, R. E., Leary, J. F., Gorenstein, D. G., 2003. Immunofluorescence assay and flow-cytometry selection of bead-bound aptamers. Nucleic Acids Res. 31, e54.

Ylera, F., Lurz, R., Erdmann, V. A., Furste, J. P., 2002. Selection of RNA aptamers to the Alzheimer's disease amyloid peptide. Biochem. Biophys. Res. Commun. 290, 1583-1588.

Yoshida, W., Sode, K., Ikebukuro, K., 2006. Aptameric enzyme subunit for biosensing based on enzymatic activity measurement. Anal. Chem. 78, 3296-3303.

Than, L. S., Zhuo, H. L., Wang, H. Z., Peng, J. C., Wang, Q. L., 2005. Screening and characterization of aptamers of hepatitis C virus NS3 helicase. Progr. Biochem. Biophys. 32, 245-250.

Zolotukhin, A. S., Michalowski, D., Smulevitch, S., Felber, B. K., 2001. Retroviral constitutive transport element evolved from cellular TAP(NXF1)-binding sequences. J. Virol. 75, 5567-5575.

Zuker, M., 2003. Mfold web server for nucleic acid folding and hybridization prediction. Nucleic Acids Res. 31, 3406-3415.

---

What is claimed is:

1. A method of identifying nucleic acid aptamers for a target molecule comprising:

obtaining an at least partially purified target molecule;

obtaining a nucleic acid ligand library, said nucleic acid ligand library comprising a plurality of nucleic acid molecules;

mixing the target molecule with the nucleic acid ligand library such that the target molecule binds to one or more aptamers present in the nucleic acid ligand library;

digesting unbound nucleic acid molecules with one or more nucleases;

separating the nucleic acid molecules bound to the target molecule from at least a portion of the unbound nucleic acid molecules, wherein said separation is accomplished by:

a) digesting unbound nucleic acid molecules; or b) digesting unbound nucleic acid molecules in combination at least one physical separation means;

disassociating the target molecule from the one or more nucleic acid molecules; and amplifying separated nucleic acid molecules;

wherein the nucleic acid ligand library comprises a plurality of nucleic acid molecules comprising the sequence 5'-$Z_x$—$N_x$—$Z'_x$-3', where N is A, G, C, T or, in the case of RNA, U, and where x is an integer from about 5 to about 100, or larger, where Z and Z' is A, G, C, T or, in the case of RNA, U, and where $Z_x$ and $Z'_x$ are complementary, or substantially complementary, to each other, and where $Z_x$ and $Z'_x$ form secondary structure;

wherein the nucleic acid ligand library comprises a plurality of nucleic acid molecules comprising the sequence 5'-TTTGGGGGGGGTTTTTTTGGG-$N_x$-CCCAAAAAAAACCCCCCCAAA-3' (SEQ ID NOs: 1 and 2, respectively), where N is A, T, G, or C, where N is A, G, C, T or, in the case of RNA, U, where x is an integer from about 5 to about 100, or larger, where the sequence 5'-TTTGGGGGGGGTTTTTTTGGG-3' (SEQ ID NO:1) is the $Z_x$ structure, and where the sequence 5'-CCCAAAAAAAACCCCCCCAAA-3' (SEQ ID NO:2) is the complementary $Z'_x$ structure.

2. A method of identifying nucleic acid aptamers for a target molecule comprising:

obtaining an at least partially purified target molecule;

obtaining a nucleic acid ligand library, said nucleic acid ligand library comprising a plurality of nucleic acid molecules;

mixing the target molecule with the nucleic acid ligand library such that the target molecule binds to one or more aptamers present in the nucleic acid ligand library;

digesting unbound nucleic acid molecules with one or more nucleases;

separating the nucleic acid molecules bound to the target molecule from at least a portion of the unbound nucleic acid molecules, wherein said separation is accomplished by:

a) digesting unbound nucleic acid molecules; or b) digesting unbound nucleic acid molecules in combination at least one physical separation means;

disassociating the target molecule from the one or more nucleic acid molecules; and amplifying separated nucleic acid molecules;

wherein the nucleic acid ligand library comprises a plurality of nucleic acid molecules comprising the sequence 5'-$Z_x$—$N_x$—$Z'_x$-3', where N is A, G, C, T or, in the case of RNA, U, and where x is an integer from about 5 to about 100, or larger, where Z and Z' is A, G, C, T or, in the case of RNA, U, and where $Z_x$ and $Z'_x$ are complementary, or substantially complementary, to each other. And where $Z_x$ and $Z'_x$ form secondary structure;

wherein the nucleic acid ligand library comprises a plurality of nucleic acid molecules comprising the sequence 5'-TTTGGGGGGGGATCCTTTTTGGG-$N_x$-CCCAAAAAGGATCCCCCCCAAA-3' (SEQ ID NOs: 3 and 4 respectively), where N is A, T, G, or C. where N is A, G, C, T or, in the case of RNA, U, where x is an integer from about 5 to about 100, or larger, where the sequence 5'-TTTGGGGGGGGATCCTTTTTGGG-3' (SEQ ID NO:3) is the $Z_x$ structure, and where the sequence 5'-CCCAAAAAGGATCCCCCCCAAA-3' (SEQ ID NO:4) is the $Z'_x$ structure, and where $Z_x$ and $Z'_x$ form complementary secondary structure that includes a BamHI restriction enzyme site.

3. The method in accordance with claim 2, where the undigested nucleic acid can be amplified by PCR utilizing the primer, 5'-TTTGGGGGGGGATCCTTTTTGGG-3' (SEQ ID3), or segment thereof, or other complementary, or substantially complementary, primers.

4. The method in accordance with claims 1 or 2, wherein the mixing step is carried out at substantially room temperature for up to about 5 hours.

5. The method in accordance with claims 1 or 2, wherein the mixing step is carried out in a binding buffer, said binding buffer comprising one of a physiologically hypertonic aqueous solution, a physiologically hypotonic aqueous solution, or a physiologically isotonic aqueous solution and wherein the pH of said binding buffer is between about 6 to about 8.

6. The method in accordance with claim 5, wherein the binding buffer comprises at least one composition selected from the list consisting of Tris, NaCl, KCl, $CaCl_2$, and tRNA, or combinations thereof.

7. The method in accordance with claim 5, wherein the binding buffer comprises from about 1 mM to about 100 mM Tris, from about 10 mM to about 500 mM NaCl, from about 0.5 mM to about 50 mM KCl, from about 0.1 mM to about 10 mM $CaCl_2$ and about 10 mg/ml tRNA.

8. The method in accordance with claims 1 or 2, further comprising liberating the aptamer from the target molecule wherein said liberating step comprises heat denaturation and a temperature up to about 100° C.

9. The method in accordance with claim 8, wherein the liberated aptamer is optionally subjected to one or more rounds of additional selection, wherein each successive round of selection is performed under increased stringency.

10. The method in accordance with claims 1 or 2, wherein one or more of the nucleases is selected from the list consisting of DNAses, RNAses, Type-II Restriction Enzymes (for example Bam-HI), Exonuclease I, Exonuclease III, and Exonuclease T, T7 Exonuclease, Klenow (5'→3' exo⁻), Lambda Exonuclease, Mung Bean Nuclease, Microccocal Nuclease, RecJf, and Nuclease BAL-31.

11. The method in accordance with claims 1 or 2, wherein the digesting step is carried out with one or more of DNAses, RNAses, Type II Restriction Enzymes (BamHI as a non-limiting example), Exonuclease I, Exonuclease III, and Exonuclease T, T7 Exonuclease, Klenow (5'→3' exo⁻), Lambda Exonuclease, Mung Bean Nuclease, Microccocal Nuclease, RecJf, and Nuclease BAL-31, or combinations thereof.

12. The method in accordance with claim 11, wherein after the digestion is complete, the nucleases are either inactivated by heat or removed by physical separation.

13. The method in accordance with claim 12, wherein the physical separation means is selected from the list consisting of affinity chromatography, biotin/avidin, antibody affinity chromatography, metal ion affinity chromatography, fusion protein chromatography, size exclusion chromatography, filtration, magnetic bead separation, centrifugation, chemical extraction, or combinations thereof.

14. The method in accordance with claims 1 or 2, wherein selected aptamers are "capped" by incorporating a di-deoxynucleotide at the 3' terminus, thereby affording in vivo protection from nuclease digestion.

15. The method in accordance with claim 1, where the undigested nucleic acid can be amplified by PCR utilizing the primer, 5'-TTTGGGGGGGGTTTTTTTGGG-3' (SEQ ID1), or segment thereof, or other complementary, or substantially complementary, primers.

16. The method in accordance with claim 1 or 2, wherein the physical separation means is selected from the list consisting of affinity chromatography, biotin/avidin, antibody affinity chromatography, metal ion affinity chromatography, fusion protein chromatography, size exclusion chromatography, filtration, magnetic bead separation, centrifugation, chemical extraction, or combinations thereof.

* * * * *